(12) United States Patent
Nakamura

(10) Patent No.: US 6,865,472 B2
(45) Date of Patent: Mar. 8, 2005

(54) VEHICLE-INSTALLED EXHAUST GAS ANALYZING APPARATUS

(75) Inventor: Hiroshi Nakamura, Kyoto (JP)

(73) Assignee: Horiba Ltd., Kyoto (JP)

( * ) Notice: Subject to any disclaimer, the term of this patent is extended or adjusted under 35 U.S.C. 154(b) by 0 days.

(21) Appl. No.: 10/627,243

(22) Filed: Jul. 25, 2003

(65) Prior Publication Data

US 2004/0064243 A1 Apr. 1, 2004

(30) Foreign Application Priority Data

Sep. 27, 2002 (JP) .......................... 2002-282994
Sep. 27, 2002 (JP) .......................... 2002-283027
Oct. 23, 2002 (JP) .......................... 2002-308761

(51) Int. Cl.[7] .............................. B60T 7/12; G05D 1/00
(52) U.S. Cl. ....................... 701/108; 701/109; 701/111; 701/112; 73/23.2; 73/23.31; 60/274; 60/277; 60/278
(58) Field of Search ................................ 701/108–112; 73/23.2–23.31; 60/274–278

(56) References Cited

U.S. PATENT DOCUMENTS 5,083,427 A * 1/1992 Anderson .................... 60/274
6,148,656 A * 11/2000 Breton ...................... 73/23.31
6,382,014 B1 * 5/2002 Breton ...................... 73/23.31
6,412,333 B2 * 7/2002 Inoue et al. ................. 73/23.2

* cited by examiner

Primary Examiner—Willis R. Wolfe
Assistant Examiner—Johnny H. Hoang
(74) Attorney, Agent, or Firm—Brooks Kushman P.C.

(57) ABSTRACT

A vehicle-installed exhaust gas analyzing apparatus includes a nondispersive infrared (NDIR) type gas analyzer for continuously measuring concentration of hydrocarbon (HC) in an exhaust gas flowing through an exhaust pipe which is connected to an engine, an exhaust gas flowmeter for continuously measuring flow rate of the exhaust gas flowing through the exhaust pipe, and an operation processing device for processing outputs from the NDIR type gas analyzer and the exhaust gas flowmeter to continuously calculate mass of total hydrocarbon (THC) contained in the exhaust gas. The components are configured so at to be installable in vehicle. THC concentration is obtained by multiplying a measurement result obtained by the NDIR type analyzer by a predetermined conversion factor.

7 Claims, 16 Drawing Sheets

VEHICLE-INSTALLED EXHAUST GAS ANALYZING APPARATUS

BACKGROUND OF THE INVENTION

1. Field of the Invention

The present invention relates to a vehicle-installed exhaust gas analyzing apparatus capable of real time measuring concentration of hydrocarbons (HC) contained in exhaust gas emitted from an engine of a vehicle such as automobile running on the road. The present invention also relates to a vehicle-installed exhaust gas analyzing apparatus for continuously measuring mass of total hydrocarbon (THC) (mass emission) contained in exhaust gas from an engine of a vehicle such as automobile. Furthermore, the present invention relates to a vehicle-installed exhaust gas analyzing apparatus equipped with a differential pressure type flowmeter such as Pitot tube type flowmeter.

2. Background Art

In recent years, increasing concerns about influence of exhaust gas emitted from engines etc. (hereinafter, simply referred to as exhaust gas) on the environment have raised the trend that the actual condition should be grasped in a condition similar to the actual environment rather than in laboratory or test course. Researches and developments (seeking) for procedures of measuring components emitted from a vehicle running on the road such as nitrogen oxides (NOx), carbon monoxide (CO), carbon dioxide ($CO_2$) and the like have been carried out. Also in the trend, it is requested to measure not only concentration of each component, but also mass emission thereof. One example that satisfies the above requirement is a vehicle-installed engine exhaust gas analyzer described in Japanese Unexamined Patent Publication 2001-124674. According to this vehicle-installed engine exhaust gas analyzer, it is possible to continuously and simultaneously measure a plurality of components such as CO, $CO_2$, NO, $N_2O$, $H_2O$, $NH_3$ and HCHO contained in exhaust gas emitted from a vehicle on the actual road. Furthermore, the above vehicle-installed engine exhaust gas analyzer is equipped therein with an exhaust gas concentration analyzing device for analyzing component concentration in exhaust gas, and an exhaust gas flow rate measuring device wherein a predetermined amount of known concentration of trace gas is injected from the upstream side of the measurement point by this exhaust gas concentration analyzing device, and the flow rate of the exhaust gas is obtained from the injection concentration and injection flow rate of the trace gas injected into the exhaust gas, whereby mass emission of the components contained in the exhaust gas is determined based on the component concentration obtained by the exhaust gas concentration analyzing device and the exhaust gas flow rate obtained by the exhaust gas flow rate measuring device.

By the way, in the field of exhaust gas analysis, requests for real-time quantitative analysis of HC have been increased in recent years. In the aforementioned vehicle-installed engine exhaust gas analyzer, however, since a Fourier transform infrared analyzer (FTIR) is used for component analysis, measurement of THC is difficult, the equipment is bulky and expensive, so that it is not suited for use on board. On the other hand, as an apparatus for measuring THC concentration, a method that uses a flame ionization detector (FID) is known. Since this FID method provides excellent stability and response in proportion to the number of contained carbons, it has been conventionally used for analyzing THC concentration contained in atmospheric air or in combustion gas emitted from a combustion apparatus such as boiler.

In the above FID method, however, an operation gas such as fuel hydrogen or supporting air is required for analysis, so that there is a problem that it is not suited for vehicle-installed application wherein compact size and measurement with simple operation are requested.

The present invention was devised in consideration of these facts, and it is an object of the present invention to provide a vehicle-installed exhaust gas analyzing apparatus capable of readily measuring THC concentration and mass in the exhaust gas in a vehicle running on an actual road.

Furthermore, according to the aforementioned vehicle-installed engine exhaust gas analyzing apparatus, though it is possible to continuously measure concentration and mass of a specific component contained in exhaust gas, it is necessary to mount a trace gas source in the vehicle and inject trace gas into the exhaust pipe while measuring the trace gas from an appropriate position for measuring exhaust gas flow rate by means of the exhaust gas flow rate measuring device, so that configuration for measuring exhaust gas flow rate is complicated. Furthermore, when the exhaust gas flow rate measuring device is used in combination with the exhaust gas concentration analyzing device, problems of deviation in time axis and difference of response between these devices arise, so that an accurate flow rate is not usually obtained. Therefore, it is impossible to accurately determine mass of every component to be measured contained in the exhaust gas.

The present invention was devised in consideration of these facts, and it is an object of the present invention to provide a vehicle-installed exhaust gas analyzing apparatus capable of continuously measuring THC mass contained in the exhaust gas in a vehicle running on an actual road with simple configuration and with high accuracy.

As one example of differential pressure type flowmeter for measuring flow rate of gas flowing through a pipe, a Pitot tube type flowmeter is well known. In a Pitot tube type flowmeter, gas flow rate (in terms of normal state) $Q_g$ (t) [$m^3$/min] can be represented by the following formula (7):

$$Q_g(t) = K \times \sqrt{\frac{P_g(t)}{101.3} \times \frac{293.15}{T_g(t)} \times \frac{\Delta h(t)}{\gamma_g}} \quad (7)$$

(wherein K: proportion coefficient

Pg (t): gas pressure [kPa]

$T_g$ (t): gas temperature [° K]

Δh (t): differential pressure of Pitot tube $\gamma_g$: gas density in normal state [g/$m^3$]

That is, by determining the proportion coefficient K in advance, it is possible to obtain flow rate of the gas from the temperature and pressure of the gas flowing through the pipe and measurement of differential pressure of the Pitot tube.

By the way, since a Pitot tube type flowmeter utilizes the fact that flow rate and square root of differential pressure has a proportional relationship as can be seen from the above formula (7), a differential manometer having wide range is required for measuring the dynamically-varying flow rate. For example, a range of 10000 times is required with respect to a flow rate range of 100 times. Also, as is the case of exhaust gas from an automobile engine, when the flow rate rapidly varies dynamically, it is impossible to average the data. Furthermore, when the engine is in idle state, the differential manometer is influenced by pulsation of the exhaust gas even though the flow rate is low, making measurement extremely difficult. In such a case, there arises another problem that response speed in high flow rate zone is decreased in compensation for attempt to ensure measurement accuracy in low flow rate zone.

For this reason, conventionally, dynamic range was often measured by using several kinds of flowmeters of different ranges as described in Japanese Unexamined Patent Publication 2001-41787, for example. However, in such a manner, a space for installing the plurality of flowmeters is required and the cost rises, and correlation among the plurality of flowmeters often raised a problem.

The present invention was devised in consideration of the facts as described above, and it is an object of the invention to provide a vehicle-installed exhaust gas analyzing apparatus including a differential pressure type flowmeter having a wide measurement range capable of securely reducing the noise in low flow rate zone without reducing the response speed in high flow rate zone, namely, capable of continuously measuring gas flow rate at desired response speed and with high accuracy from low flow rate zone to high flow rate zone.

SUMMARY OF THE INVENTION

In the present invention, means for achieving the aforementioned objects are configured as follows.

That is, in a vehicle-installed exhaust gas analyzing apparatus according to claim 1, a nondispersive infrared (NDIR) type gas analyzer for continuously measuring concentration of hydrocarbon (HC) in an exhaust gas flowing through an exhaust pipe which is connected to an engine, an exhaust gas flowmeter for continuously measuring flow rate of the exhaust gas flowing through the exhaust pipe, and an operation processing device for processing outputs from the NDIR type gas analyzer and the exhaust gas flowmeter to continuously calculate mass of total hydrocarbon (THC) contained in the exhaust gas are configured so at to be installable in vehicle, wherein THC concentration is obtained by multiplying a measurement result obtained by the NDIR type analyzer by a predetermined conversion factor.

There are plural kinds of HCs contained in exhaust gas, and it is known that when concentrations of these plural kinds of HC components are measured by means of the NDIR type gas analyzer, the relative sensitivity varies among different HC components as shown in FIG. 6.

Then HC concentration derived by measurement of HC concentration using the NDIR type gas analyzer (hereinafter, referred to as NDIR-HC) is outputted in terms of hexane (n-C6H14), namely as a concentration of hexane (ppm). On the other hand, HC concentration derived by measurement of HC concentration using FID (hereinafter referred to as FID-HC) is ppmC. As a result of repeatedly conducting a variety of experiments, the inventors of the present application found that there is a certain relationship between said NDIR-HC and FID-HC.

FIG. 7 shows a graph plotting NDIR-HC and FID-HC when different kinds of automobiles are driven in different driving modes, and it was found that FID-HC (represented by "y") and NDIR-HC (represented by "x") have the following relationship:

$$y = 1.66x \quad (1)$$

That is, by multiplying NDIR-HC by a conversion factor, 1.66, the value corresponding to FID-HC can be obtained according to the following formula (2):

$$FID\text{-}HC \approx \text{conversion factor} \times (NDIR\text{-}HC) \times 6 \times Q/L \quad (2)$$

(wherein Q: total flow of exhaust gas (L), L: driving distance (km))

FIGS. 8 and 9, respectively show temporal change of emission concentration of THC of diesel car and gasoline car, in each of which the top stage represents NDIR-HC, middle stage FID-HC and bottom stage driving mode. From these drawings, validity of the relationship represented by the formula (1) is verified.

FIG. 10 shows comparison between HC emission amount obtainable by a modal mass measuring method using HC meter based on the FID method, and that obtainable by CVS (constant volume gas sampling) method commonly used heretofore, and FIG. 11 shows comparison between HC emission amount obtainable by On-Board Emission Measurement System (OBS) using the vehicle-installed exhaust gas analyzing apparatus according to the present invention, namely, HC emission amount obtainable by the vehicle-installed exhaust gas analyzing apparatus according to the present invention, and HC emission amount obtainable by CVS method. This proved that both of measurement by means of HC meter based on FID method and measurement by OBS have 1:1 correlation with measurement by general CVS method.

In the vehicle-installed exhaust gas analyzing apparatus according to the present invention having the above configuration, since FID method is not used for measurement of HC concentration, it is not necessary to provide operation gas such as fuel hydrogen or supporting air, so that it is possible to configure the entire apparatus smaller and more compact. Although in the HC analysis based on the NDIR method, the relative sensitivity varies depending on the specific component of HC, by using an appropriate conversion factor with respect to a specific component (hexane in the present application), it is possible to readily calculate THC emission amount. Therefore, according to the aforementioned vehicle-installed exhaust gas analyzing apparatus, it is possible to readily measure THC contained in exhaust gas in a running vehicle.

Furthermore, for achieving the aforementioned objects, a vehicle-installed exhaust gas analyzing apparatus according to claim 2 is characterized in that a Pitot tube type flowmeter is used as said exhaust gas flowmeter, and said operation processing device is configured to continuously calculate said emission mass of THC using respective output signals of said Pitot tube type flowmeter and NDIR type analyzer as well as an exhaust gas temperature signal and an exhaust gas pressure signal in the vehicle-installed exhaust gas analyzing apparatus according to claim 1.

According to the above vehicle-installed exhaust gas analyzing apparatus, it is not necessary to arrange a trace gas source, a device for measuring an amount of introduced trace gas and the like in the vehicle, so that mass of a specific compound to be measured contained in the exhaust gas can be measured continuously and accurately with simple configuration.

And in the vehicle-installed exhaust gas analyzing apparatus according to claim 2, a device for removing influence of pressure change due to pulsation and the like of a buffer tank, capillary or the like may be provided between a differential manometer and a Pitot tube for static pressure detection and a Pitot tube for dynamic pressure detection of the Pitot tube type flowmeter (claim 3). According to this configuration, even when an exhaust gas flowing through the exhaust pipe pulses, since the change in pressure due to this pulsation is eliminated by the above-mentioned buffer tank or the like, it is possible to successfully eliminate the influence of said pulsation and accurately measure the flow rate of the exhaust gas.

Furthermore, in the vehicle-installed exhaust gas analyzing apparatus according to claim 2, the Pitot tube for static pressure detection and the Pitot tube for dynamic pressure detection may be provided in a tailpipe attachment which is freely connectable/detachable to/from the exhaust pipe (claim 4). According to this configuration, the Pitot tube for static pressure detection and the Pitot tube for dynamic pressure can be readily handled and attachment/detachment of these members to/from the exhaust pipe can be readily executed.

In order to achieve the objects described above, the vehicle-installed exhaust gas analyzing apparatus according to claim 5 is characterized in that as the exhaust gas flowmeter, a differential pressure type flowmeter which is adapted to detect a differential pressure in the gas flowing through the exhaust pipe by means of a differential manometer and subject a differential pressure signal outputted from the differential manometer to an arithmetic process, thereby obtaining flow rate of the gas is used; the differential pressure signal is sampled every certain time; and moving-average is employed for improving S/N in the vehicle-installed exhaust gas analyzing apparatus according to claim 1. In executing moving-average on these plurality of sampled data, the number of data to be subjected to the moving-average is not fixed, but changed in accordance with the flow rate. That is, the number is small in high flow rate zone where S/N is large, while the number is large in low flow rate zone.

In the above Pitot tube type flowmeter (differential pressure type flowmeter), a differential pressure signal outputted from the differential manometer is sampled every certain time, a predetermined number of data is stored, and when subjecting these sampled plural data to moving-average, the number of data to be subjected to the moving-average is changed in accordance with the flow rate. Therefore, a wide flow rate range is realized without decreasing the response speed in high flow rate zone where influence is large when calculating the emission amount of exhaust gas component from exhaust gas flow rate as is the case of engine exhaust gas analysis, for example.

In the vehicle-installed exhaust gas analyzing apparatus according to claim 5, the number of data to be subjected to the moving-average may be varied in multi stages (claim 6). That is, in the vehicle-installed exhaust gas analyzing apparatus according to claim 6, defining the data obtained by converting an indicative value of the differential manometer into a pressure unit as x and an arbitrary number as Y, data of the number corresponding to $[Y/(\Sigma x+1)]$: Gauss symbol) is moving-averaged.

In the above vehicle-installed exhaust gas analyzing apparatus, since the number of data used for moving-average is large in low flow rate zone and the number of data used for moving-average is small in high flow rate zone, even if pulsation occurs in the gas flow to cause variation of differential pressure, by taking data of longer than the cycle of the variation, it is possible to eliminate the influence caused by the variation in differential pressure.

Also, in the vehicle-installed exhaust gas analyzing apparatus according to claim 5, defining the data obtained by converting an indicative value of the differential manometer into a pressure unit as x, an arbitrary number as Y, an appropriate integer as $\alpha$, and an appropriate constant as C, data of the number corresponding to $[Y/(\Sigma x)^{\alpha}+C)]$ ([ ]: Gauss symbol) may be moving-averaged, and the number of data may be automatically adjusted to a suitable value by a full scale value of the differential manometer and a flow rate of a predetermined time (claim 7).

DETAILED DESCRIPTION OF THE PREFERRED EMBODIMENTS

Figure 1:
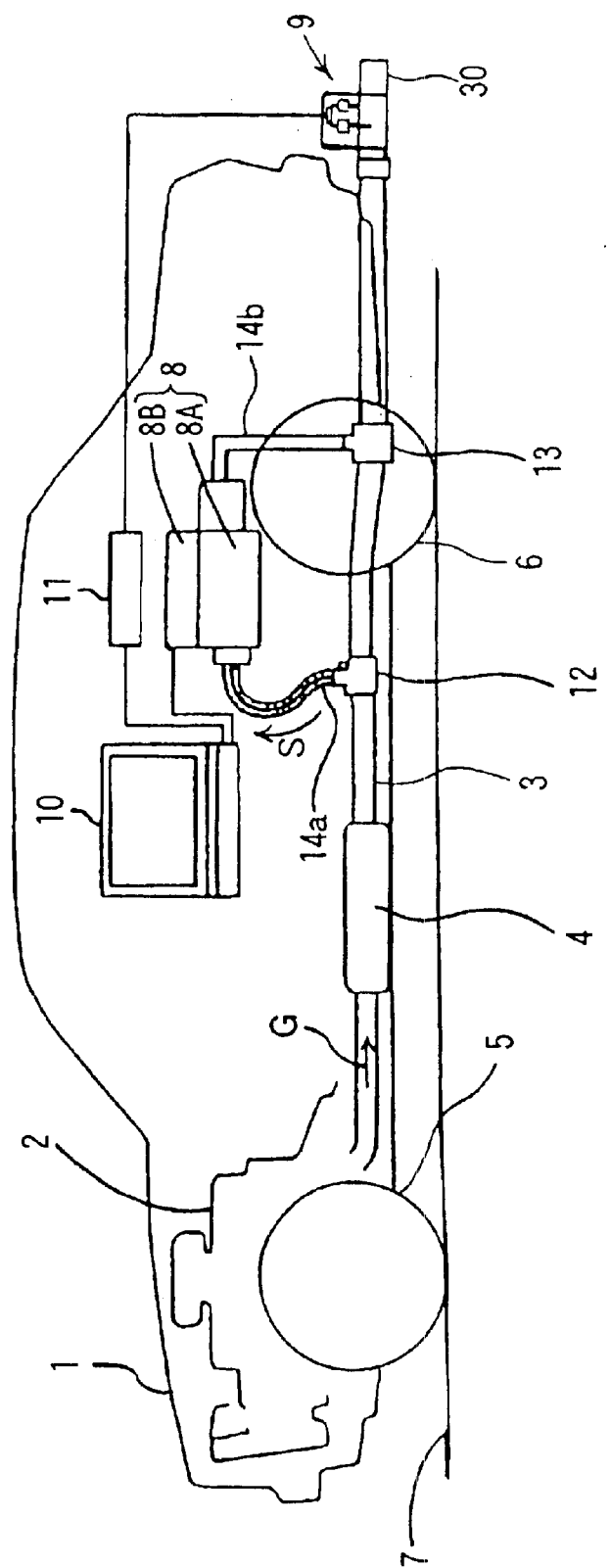
FIG. 1 is a view schematically showing a vehicle-installed exhaust gas analyzing apparatus according to the present invention installed in an automobile.

In the following, the detail of the present invention will be explained with reference to the drawings. FIGS. 1 to 5 show one example of a vehicle-installed exhaust gas analyzing apparatus according to the present invention. First FIG. 1 shows an embodiment in which said vehicle-installed exhaust gas analyzing apparatus is installed in an automobile, and in this view, the reference numeral 1 denotes an automobile serving as a vehicle to be subjected to measurement. The reference numeral 2 denotes an engine of the automobile 1, the numeral 3 denotes an exhaust pipe connecting with the engine 2 and through which an exhaust gas G flows, the numeral 4 denotes a catalyst device provided in the exhaust pipe 3. The reference numerals 5, 6 respectively denote a front wheel and a rear wheel of the automobile 1, and the numeral 7 denotes a road surface.

Figure 2:
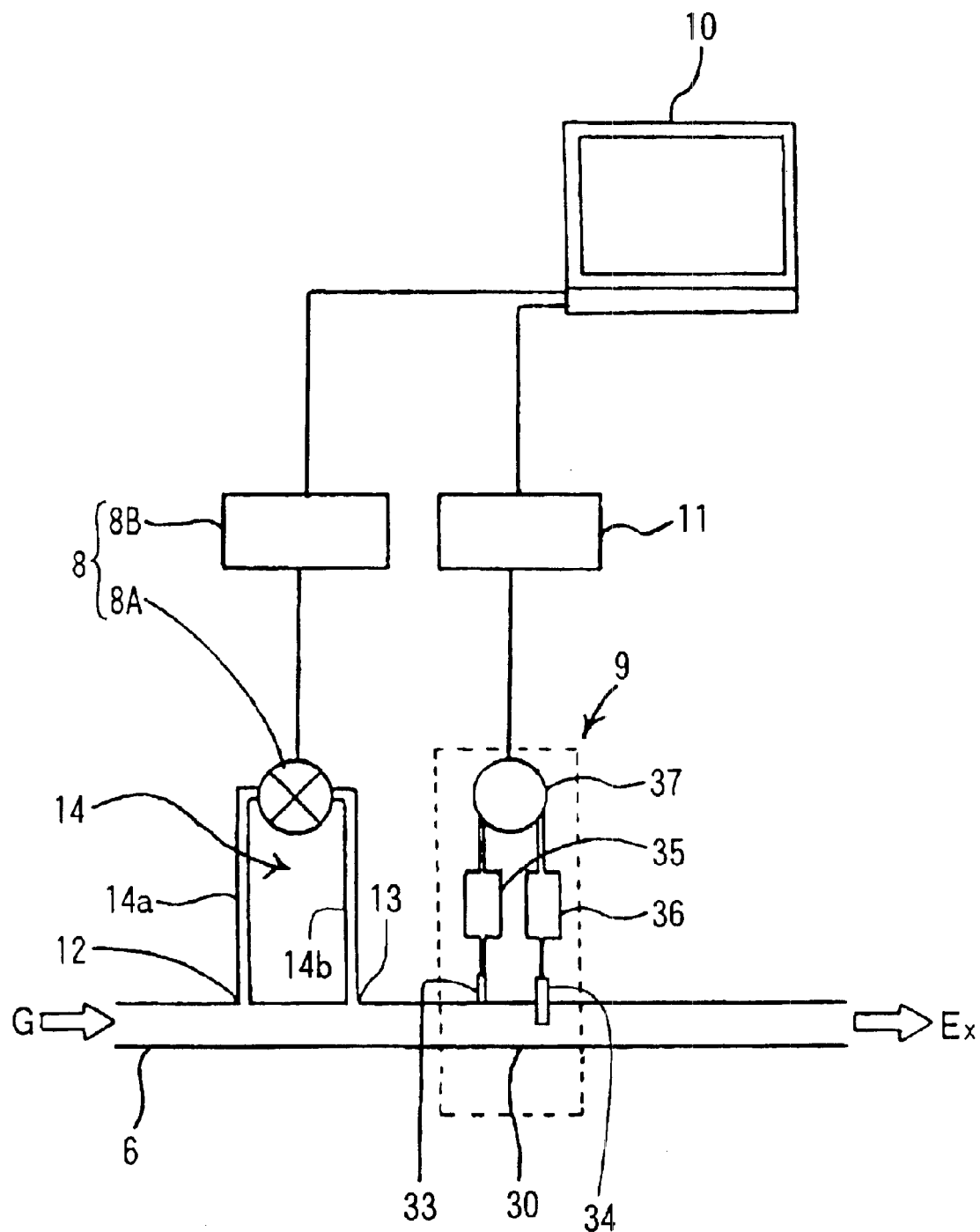
FIG. 2 is a view schematically showing one exemplary configuration of said vehicle-installed exhaust gas analyzing apparatus.

The exhaust pipe 3 is provided with an NDIR type gas analyzer 8 and an exhaust gas flowmeter 9 as shown in FIG. 2. That is, said NDIR type gas analyzer 8 is provided within the automobile 1, and composed of a gas analyzing section 8A and an operation controlling section 8B. The exhaust gas flowmeter 9 is implemented, for example, by a Pitot tube type flowmeter, and arranged so as to be attached in detachable manner to the exhaust pipe 3. The details of these arrangements for 8 and 9 will be described later. The reference numeral 10 denotes an operation processing device (such as personal computer) installed within the automobile 1, which sends/receives a signal with said operation controlling section 8B to control the entire NDIR type gas analyzer 8, or performs operation based on signals from operation controlling section 8B and the exhaust gas flowmeter 9 to calculate HC amount (mass) emitted from the engine 2, or displays various measurement results, or stores and records measurement results and the like. The reference numeral 11 denotes an interface interposed between the exhaust gas flowmeter 9 and the operation processing device 10, which is equipped with a function of converting an analog signal to a digital signal and so on. The operation processing device 10 is so configured that vehicle data such as vehicle speed, engine revolutions and the like in the automobile 1 is transmitted.

Now configuration of the above NDIR type gas analyzer 8 will be explained in detail. As shown in FIG. 2, on the downstream side of the catalyst device 4 in the exhaust pipe 3 are formed a branching connection section 12 and a converging connection section 13 as shown in FIG. 2, and between these connection sections 12 and 13 is provided a gas measuring path 14. In this gas measuring path 14, the gas analyzing section 8A of the NDIR type gas analyzer 8 is intervened. In the gas measuring path 14, the part from the branching connection section 12 to the NDIR type gas analyzer 8 is referred to as a sampling path 14a, and the part from the NDIR type gas analyzer 8 to the converging connection section 13 is referred to as a discharging path 14b.

The branching connection section 12 is configured so that it can collect a part of the exhaust gas G flowing through the exhaust pipe 3 from the engine 2 as a sample gas S. Additionally, a heater is wound around the sampling path 14a so that the sample gas S flowing therethrough is heated and maintained at a predetermined temperature. In this manner, since the sample gas S is supplied to the gas analyzing section 8A via the gas measuring path 14 under heating, even if the sample gas S contains high concentration of water, it can be measured without necessity of subjecting to dehumidifying treatment. The operation controlling section 8B is configured so that it controls individual parts of the gas analyzing section 8A in response to an instruction from the operation processing device 10 within the automobile, or calculates concentration based on an output signal of a detector (described later) of the gas analyzing section 8A.

Figure 3:
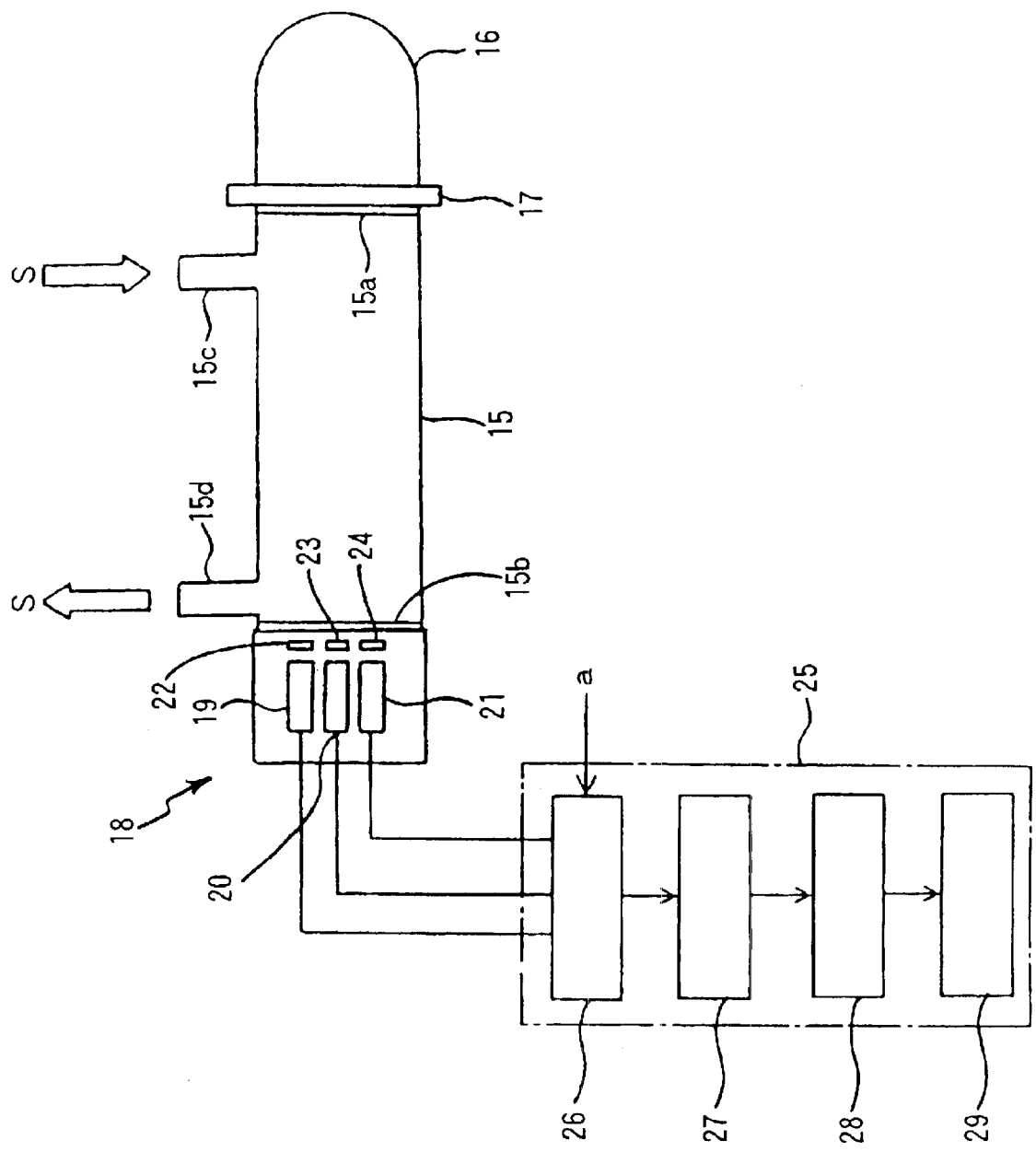
FIG. 3 is a view schematically showing one exemplary configuration of a NDIR type gas analyzer in said vehicle-installed exhaust gas analyzing apparatus.

FIG. 3 is a view schematically showing one exemplary configuration of the gas analyzing section 8A of the NDIR type gas analyzer 8, and in this drawing, the numeral 15 denotes a cell which is sealed with infrared-permeable cell windows 15a and 15b at either end and formed with an inlet 15c and an outlet 15d for the sample gas S. Although not illustrated in detail, the cell 15 is arranged to be heated so as to keep an appropriate temperature. To the gas inlet 15c is connected a downstream end of the gas sampling path 14a and to the gas outlet 15d is connected an upstream end of the discharging path 14b.

The numeral 16 denotes an infrared light source provided on the side of one cell window 15a of the cell 15, for irradiating inside of the cell 15 with an infrared beam, and the numeral 17 denotes a light chopper interposed between the infrared light source 16 and the cell 15, which is rotationally driven, for example, by a motor (not shown) to turn on/off (chop) the infrared beam emitted by the infrared light source 16 at certain cycles.

Figure 4:
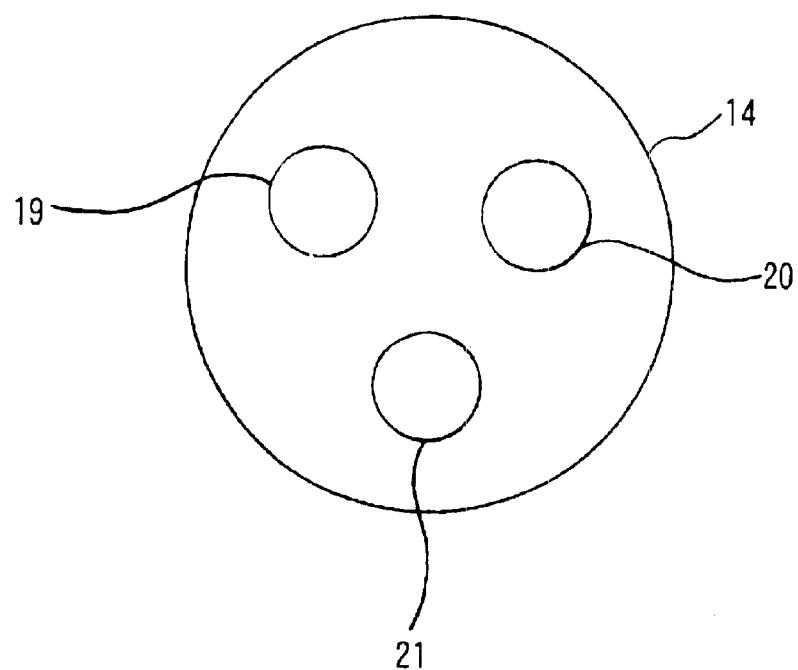
FIG. 4 is a schematic diagram showing one exemplary arrangement of an infrared detector in a detecting section of said NDIR type gas analyzer.

The numeral 18 denotes a detecting section provided on the side of the other cell window 15b of the cell 15, and consists of a plurality of infrared detectors arranged in optically parallel. In this embodiment, it consists of, for example, an HC detector 19 for detecting concentration of a plurality of HC components which are contained in the sample gas S and are object components to be measured; a moisture detector 20 for measuring moisture ($H_2O$) which is an interfering component contained in the sample gas S; a comparing detector 21; and optical filters 22 to 24 respectively provided in correspondence with light-receiving sides of the above detectors 19 to 21. As the above detectors 19 to 21, infrared detectors located at the positions which are concentric and divide the circumference into three as shown in FIG. 4 (hereinafter referred to simply as detector. In FIG. 3, they are illustrated on the same line for the sake of convenience) are used.

The above detectors 19 to 21 are implemented by, for example, semiconductor detectors. The optical filter 22 in correspondence with the HC detection 19 is implemented by a band-pass filter which allows only infrared beams within characteristic absorption band for HC to pass through, the optical filter 23 in correspondence with the moisture detector 20 is implemented by a band-pass which allows infrared beams within characteristic absorption band for $H_2O$ to pass through, the optical filter 24 in correspondence with the comparing detector 21 is implemented by a band-pass filter which allows infrared beams outside the characteristic absorption bands for HC and $H_2O$ to pass through.

The numeral 25 denotes a concentration calculating section in the operation controlling section 8B, which calculates concentration based on outputs from the detectors 19 to 21, and the numeral 26 denotes a synchronous rectification circuit, the numeral 27 denotes a smoothing circuit, the numeral 28 denotes a subtractive circuit, and the numeral 29 denotes a moisture interference/moisture coexistence influence correcting operation circuit (hereinafter, simply referred to as a correcting operation circuit). The concentration calculating section 25 calculates concentration of HC which is an objective component to be measured, and concentration of moisture which is an interfering component based on outputs from the detectors 19 to 21, and determines concentration of HC in which influence of moisture coexistence is corrected using the above concentrations.

Figure 5:
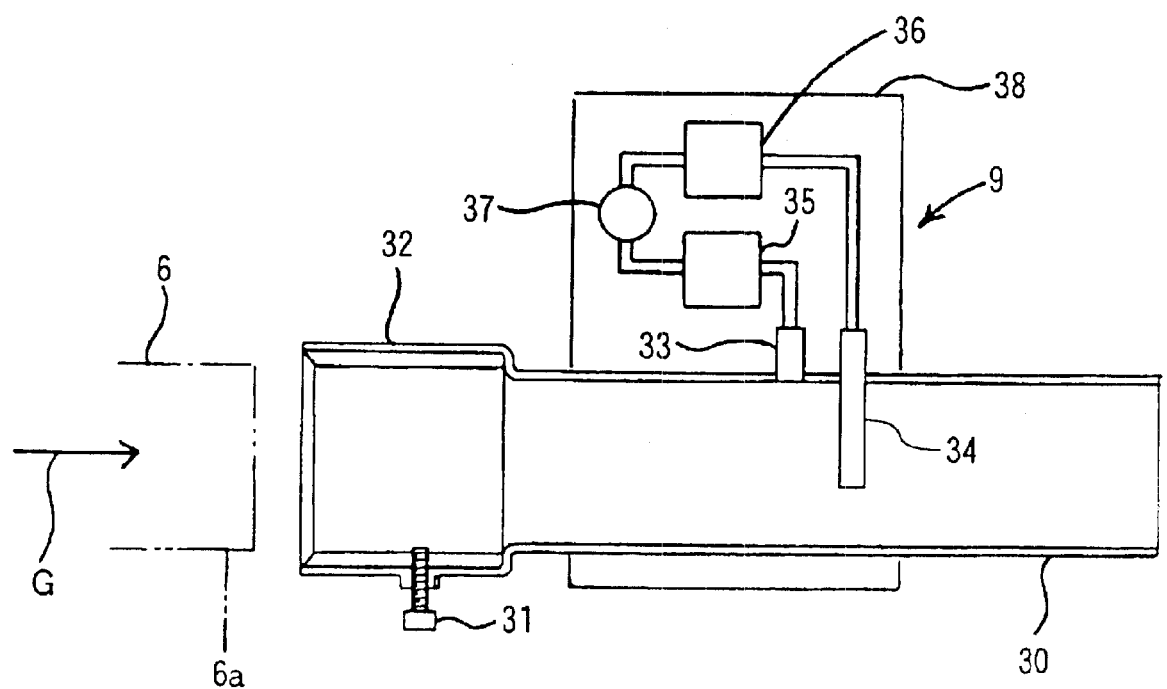
FIG. 5 is a view schematically showing one exemplary configuration of an exhaust gas flowmeter in said vehicle-installed exhaust gas analyzing apparatus.
Figure 6:
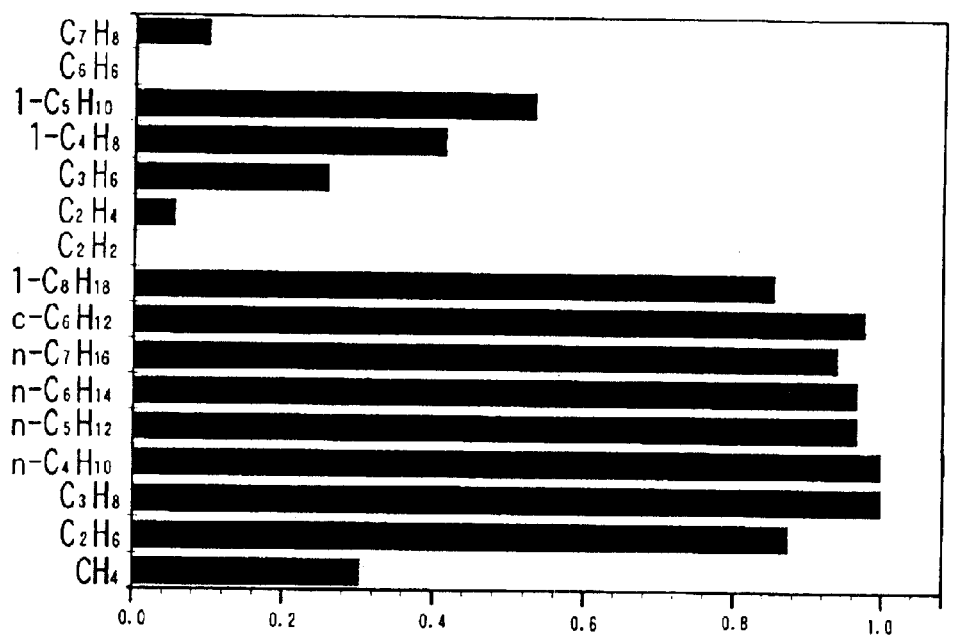
FIG. 6 is a view showing comparison of relative sensitivity for HC components in the NDIR method.
Figure 7:
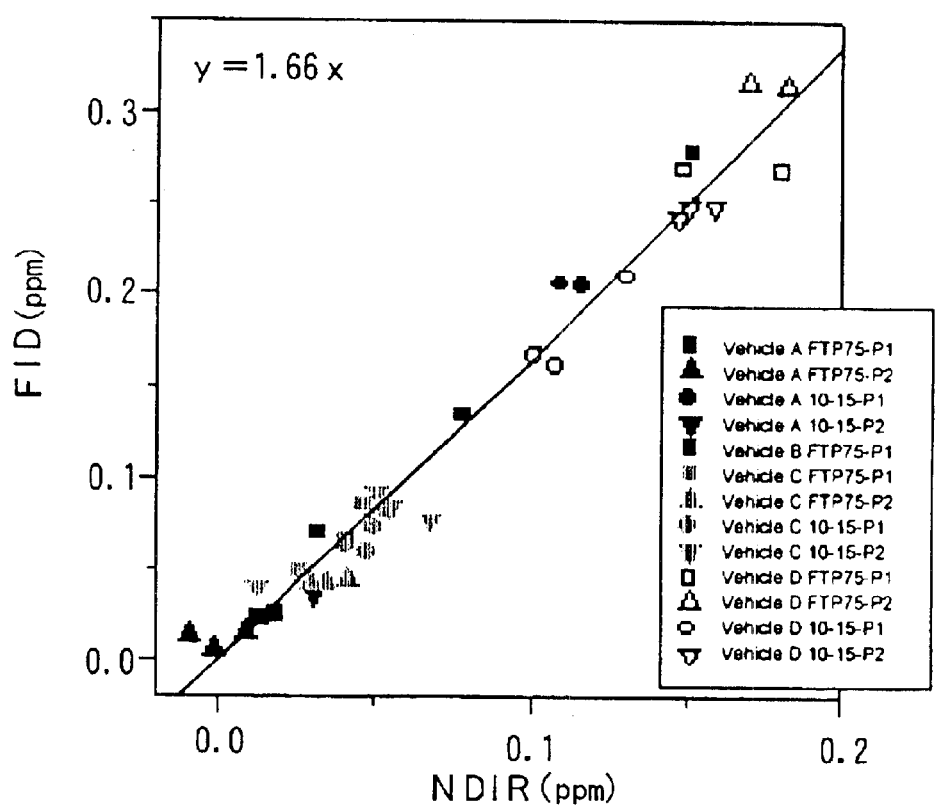
FIG. 7 is a view in which HC concentration obtained by the NDIR method and HC concentration obtained by the FID method when different kinds of automobiles are driven in different modes are plotted.
Figure 8:
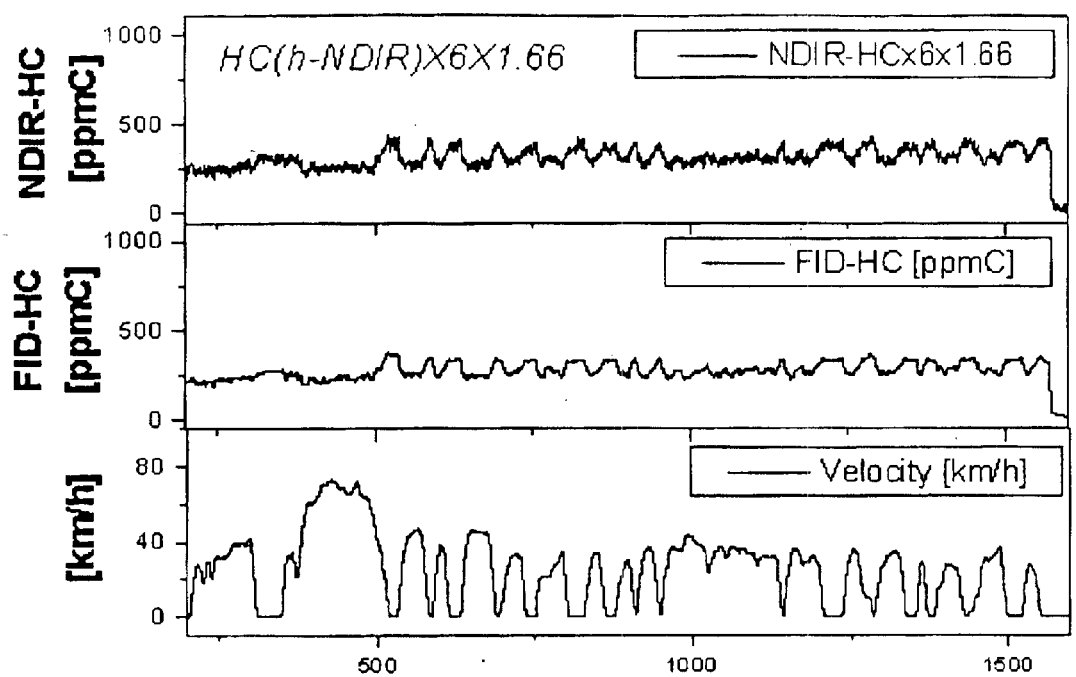
FIG. 8 is a view showing temporal change of emission concentration of THC in a diesel car.
Figure 9:
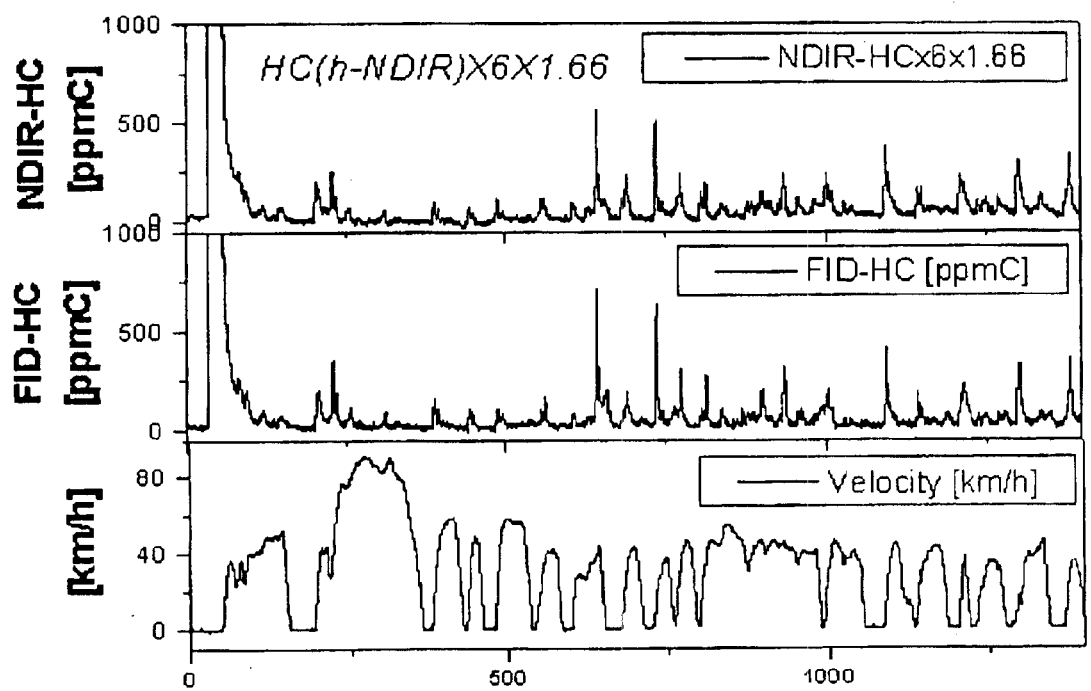
FIG. 9 is a view showing temporal change of emission concentration of THC in a gasoline car.
Figure 10:
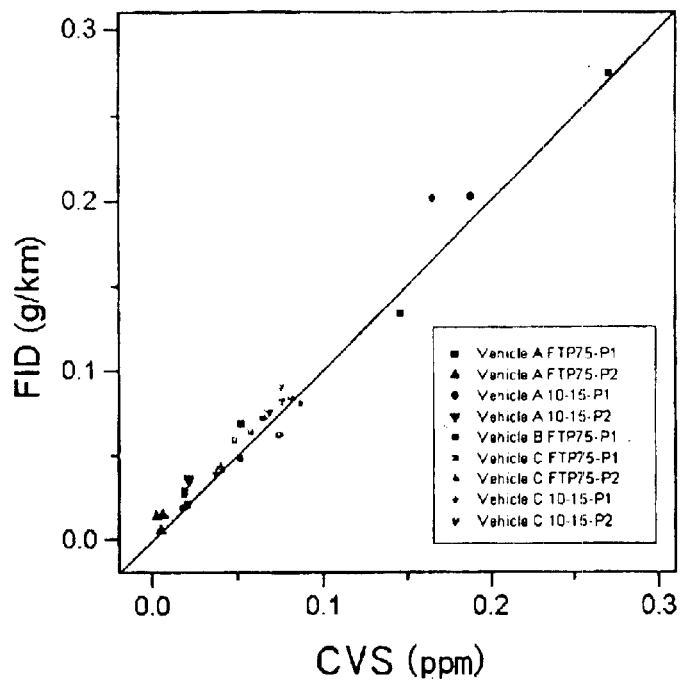
FIG. 10 is a view showing comparison of HC emission amount between the modal mass measuring method using a HC meter based on the FID method and the CVS method.
Figure 11:
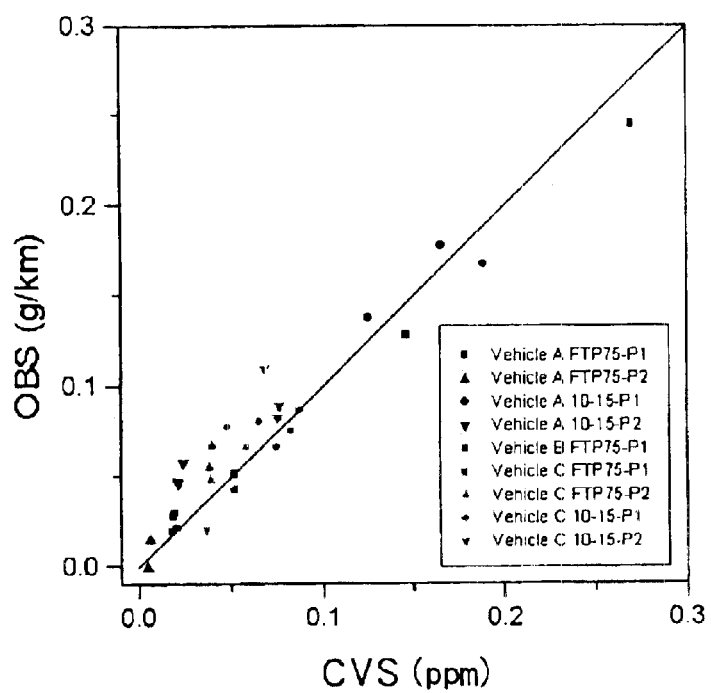
FIG. 11 is a view showing comparison between HC emission amount obtained by the vehicle-installed exhaust gas analyzing apparatus according to the present invention and HC emission amount obtained by CVS method.

FIG. 5 schematically shows configuration of the exhaust gas flowmeter 9. The numeral 30 denotes a tailpipe attachment which is detachably connected to the downstream end 6a of the exhaust pipe 3 through which the exhaust gas G from the engine 2 flows. The tailpipe attachment 30 has an inner diameter similar to that of the exhaust pipe 3 and formed at its one end with a connecting section 32 which is provided with a fixing screw 31 and is detachable fitted outside the downstream end 6a and opened at its other end. This tailpipe attachment 30 is provided with the Pitot pipe type flowmeter 9 in unit structure. That is, a Pitot tube for static pressure detection 33 is provided at the upstream position of the tailpipe attachment 30 on a tube wall 30a so as to oppose to the interior of the pipe, and a Pitot tube for dynamic pressure detection 34 is provided at a position slightly downstream the Pitot tube for static pressure detection 33 so as to be inserted in the pipe. These Pitot tubes 33 and 34 are respectively connected to a differential manometer 37 via buffer tanks 35 and 36. The reference numeral 38 denotes a casing for accommodating the aforementioned members 33 to 37 in integrated manner, and is detachably attached to the tailpipe attachment 30 by way of suitable means.

Next, operation of the vehicle-installed exhaust gas analyzing apparatus having the above configuration will be explained with reference to FIGS. 6 to 11 as well. As shown in FIG. 1, the automobile 1 is caused to run on the actual road under various conditions (for example, ascending slope, descending slope, uneven road, raining weather, sharp bend, total mass and the like). As a result of this, exhaust gas G from the engine 2 is discharged to the exhaust pipe 3, and a part of the exhaust gas G is collected as sample gas S into the gas sampling path 14a via the branching connection section 12, and supplied to the cell 15 of the gas analyzing section 8A of the NDIR type gas analyzer 8.

In this case, since the branching connection section 12 and the gas sampling path 14a are heated and maintained at appropriate temperature by means of the heater, and the cell 15 is heated and kept at appropriate temperature, it is possible to prevent components and moisture contained in the collected sample gas S from being condensed.

In the above gas analyzing section 8A, the sample gas S having passed trough the gas sampling path 14a is supplied to the cell 15, while the cell 15 is irradiated with the infrared light source 16 and the optical chopper 17 rotates at predetermined cycles, whereby AC signals corresponding to concentrations of HC and $H_2O$ and an AC signal which is a comparative signal are outputted from the detectors 19 to 21 and inputted to the synchronous rectification circuit 26.

Since a synchronous signal a for rectification based on the rotation cycle of the optical chopper 17, for example, is inputted to the synchronous rectification circuit 26, the measurement AC signals corresponding to the concentrations are synchronously rectified according to the synchronous signal a, and then subjected to smoothing operation at the smoothing circuit 27. Concentrations of HC and $H_2O$ can be obtained by subtracting the outputs of the detectors 19, 20 regarding HC and $H_2O$ from output of the comparing detector 21 at the subtractive circuit 28.

By the way, since the concentration of HC obtained by the above-described operation is influenced by moisture contained in the sample gas S, it is necessary to correct this influence by moisture, to obtain a real concentration (concentration after correction of moisture influence). In the following, an explanation will be made on principle and procedure for this concentration correction.

In general, when HC is measured in accordance with the NDIR method, moisture interference at zero point of HC meter will appear because the infrared absorption band of $H_2O$ and the infrared absorption band of HC overlap with each other. Further, at span points, influence of moisture interference and moisture coexistence are observed. The expression "influence of moisture coexistence at span" means that the degree of infrared absorption of HC changes due to coexistence of moisture in the sample gas S, and the influence of moisture coexistence is known not to depend on HC concentration, but have a certain relationship with moisture concentration. For this reason, in the NDIR type gas analyzer 8, moisture interference at zero point is corrected using moisture concentration obtained based on output of the moisture detector 20 and output of the comparing detector 21. Herein, as previously described, since HC concentration after correction of moisture interference at zero point is influenced by moisture coexistence in a certain relationship with respect to moisture concentration, influence of moisture coexistence is corrected with regard to HC concentration that has been subjected to correction for moisture interference at zero point. As a result of this, it is possible to obtain HC concentration after correction in which both the moisture interference at zero point and the moisture interference at span point are corrected.

As for the detail of elimination of influence by moisture contained in the sample gas S with respect to HC concentration described above, see Japanese Unexamined Patent Publication 2002-16635 filed by the present inventors.

In this way, in the above NDIR type gas analyzer 8, after eliminating water interference at zero with respect to HC concentration, influence of water coexistence is eliminated based on a linear relationship between moisture concentration and moisture coexistence influence, so that it is possible to measure HC concentration with high accuracy. Also, in contrast to conventional methods and apparatuses, since it is not necessary to provide a pretreatment device such as dehumidifying device, the response speed of analysis increases, and the configuration of the entire apparatus becomes compact, and hence the space, power consumption and cost can be saved. Furthermore, since measurement is conducted while heating and keeping the sample gas S to a predetermined temperature or higher, correction of moisture partial pressure is no longer required.

As described above, in the vehicle-installed exhaust gas analyzing apparatus having the above configuration, a part of the exhaust gas G from the engine 2 is partly sampled at the branching connection section 12 of the exhaust pipe 3 for measuring concentration of HC at the NDIR type gas analyzer 8 and supplied as a sample gas S to the NDIR type gas analyzer 8. This sample gas S is converged with a majority of exhaust gas G flowing through the exhaust pipe 3 at the converging connection section 13. That is, the flow rate of the exhaust gas G flowing through the exhaust pipe 3 is continuously measured by means of the exhaust gas flowmeter 9 provided in the tailpipe attachment 30 connected to the downstream end of the exhaust pipe 3.

That is, in the above exhaust gas flowmeter 9, a static pressure of the exhaust gas G flowing in the tailpipe attachment 30 via the exhaust pipe 3 is obtained by the Pitot tube for static pressure detection 33, and a sum of dynamic pressure and static pressure of the exhaust gas G is obtained by the Pitot tube for dynamic pressure detection 34. Then, the differential manometer 37 calculates a difference between the pressure detected by the Pitot tube for static pressure detection 33 and the pressure detected by the Pitot tube for dynamic pressure detection 34 to obtain a dynamic pressure of the exhaust gas G, and flow rate of the exhaust gas G is determined by performing operation based on the above dynamic pressure. And, in this case, since the pressures detected by the Pitot tube for static pressure detection 33 and by the Pitot tube for dynamic pressure detection 34 are inputted into the differential manometer 37 via the buffer tanks 35, 36, respectively, even if the exhaust gas G pulses to cause pressure change, the difference is eliminated by the buffer tanks 35 and 36, so that it is possible to derive only a pressure difference generated by change in flow rate of the exhaust gas G. Therefore, even when the exhaust gas G pulses due to change in output of the engine 2, this influence can be successfully eliminated, and flow rate of the exhaust gas G can be measured with high accuracy.

As described above, in the vehicle-installed exhaust gas analyzing apparatus in this embodiment, it is possible to continuously measure concentration of HC contained in the exhaust gas G emitted from the engine 2 by means of the NDIR type gas analyzer 8, as well as to continuously measure flow rate of the exhaust gas G by the exhaust gas flowmeter 9. Therefore, it is possible to continuously determine mass of HC (HC amount) emitted from the engine 2 by calculation from the HC concentration and flow rate of the exhaust gas.

The vehicle-installed exhaust gas analyzing apparatus performs measurement of HC concentration in accordance with the NDIR method, and hence it is not necessary to provide an operation gas such as fuel hydrogen and supporting air unlike the case of measuring concentration according to the FID method. Therefore, it is possible to design the HC concentration measuring device small and compact enough to be installed in the automobile, or vehicle-installed type, with the result that it is possible to continuously conduct measurement of exhaust gas in real time while the automobile 1 is traveling.

The exhaust gas flowmeter 9 is formed in unit form to the tailpipe attachment 30 which is freely and readily detachable with respect to the exhaust pipe 3 connecting to the engine 2 of the automobile 1, so that it is small and compact in shape. Furthermore, as is in the above embodiment, when the buffer tanks 35 and 36 are provided between the differential manometer 37, and the Pitot tube for static pressure detection 33 and the Pitot tube for dynamic pressure detection 34, even if pulsation occurs in the exhaust gas G flowing through the exhaust pipe 3, the flow rate of the exhaust gas G can be continuously measured with high accuracy without affected by such pulsation.

Therefore, according to the vehicle-installed exhaust gas analyzing apparatus comprising the above NDIR type gas analyzer 8 and the exhaust gas flowmeter 9, it is possible to continuously measure HC amount in the exhaust gas G with high accuracy.

In the above embodiment, although operations such as calculation of concentration and correction of concentration are adapted to be conducted in the NDIR type exhaust gas analyzer 8, these operations may be conducted in the operation processing device 1.

Furthermore, the exhaust gas flowmeter 9 may be implemented by the other types of flowmeters, for example Kalman flowmeter, other than the above-mentioned Pitot tube type flowmeter.

Further, the engine 2 may be installed in an automobile running in a predetermined driving mode on a chassis dynamo, or may be a stand-alone engine installed in the engine dynamo.

As explained above, according to the vehicle-installed exhaust gas analyzing apparatus of the present invention, the NDIR type gas analyzer serving as the HC concentration measuring device and the exhaust gas flowmeter serving as the exhaust gas flow rate measuring device, and the operation processing device for calculating HC mass based on outputs of the NDIR type gas analyzer and the exhaust gas flowmeter are provided in a vehicle. Therefore, the configuration is small and compact, and HC mass in exhaust gas can be readily measured in a running vehicle.

Particularly, in calculating HC concentration, by readily calculating HC emission mass using a suitable conversion factor, it is possible to determine HC mass more easily while achieving the accuracy comparable to that of conventional approach.

Figure 12:
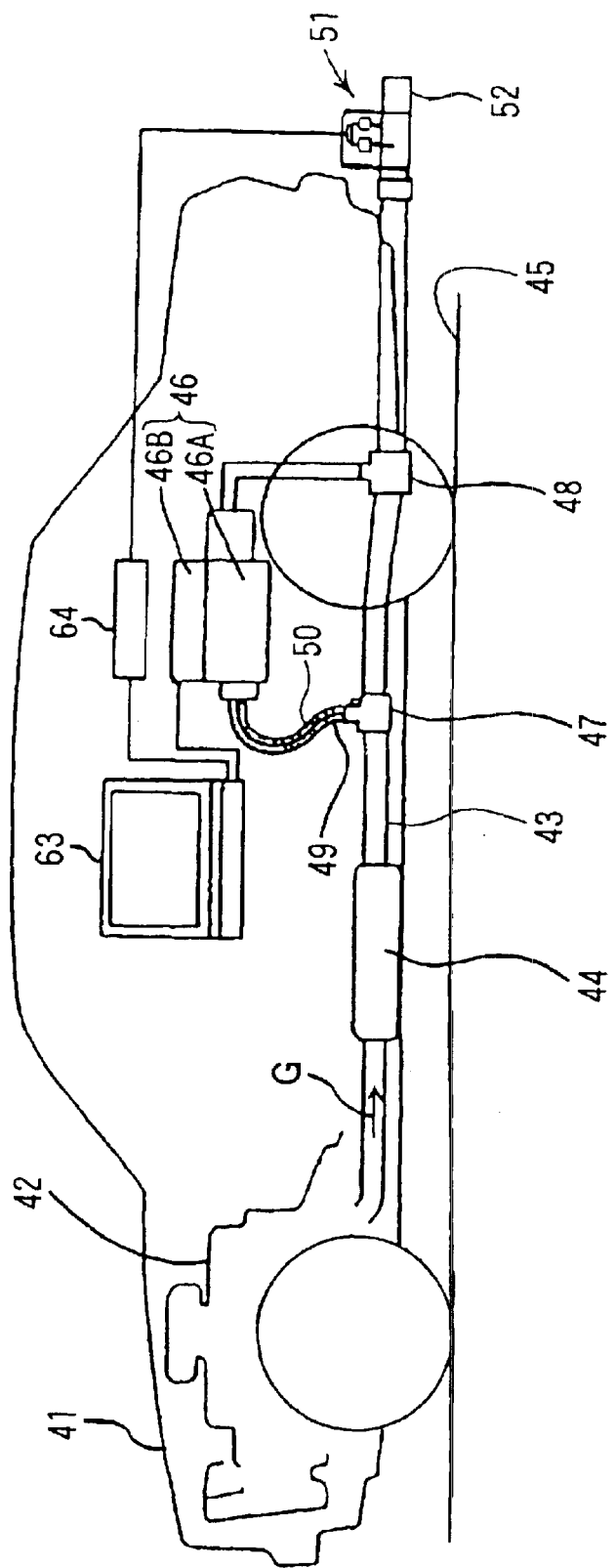
FIG. 12 is a view schematically showing a vehicle-installed exhaust gas analyzing apparatus according to the present invention installed in a car.
Figure 13:
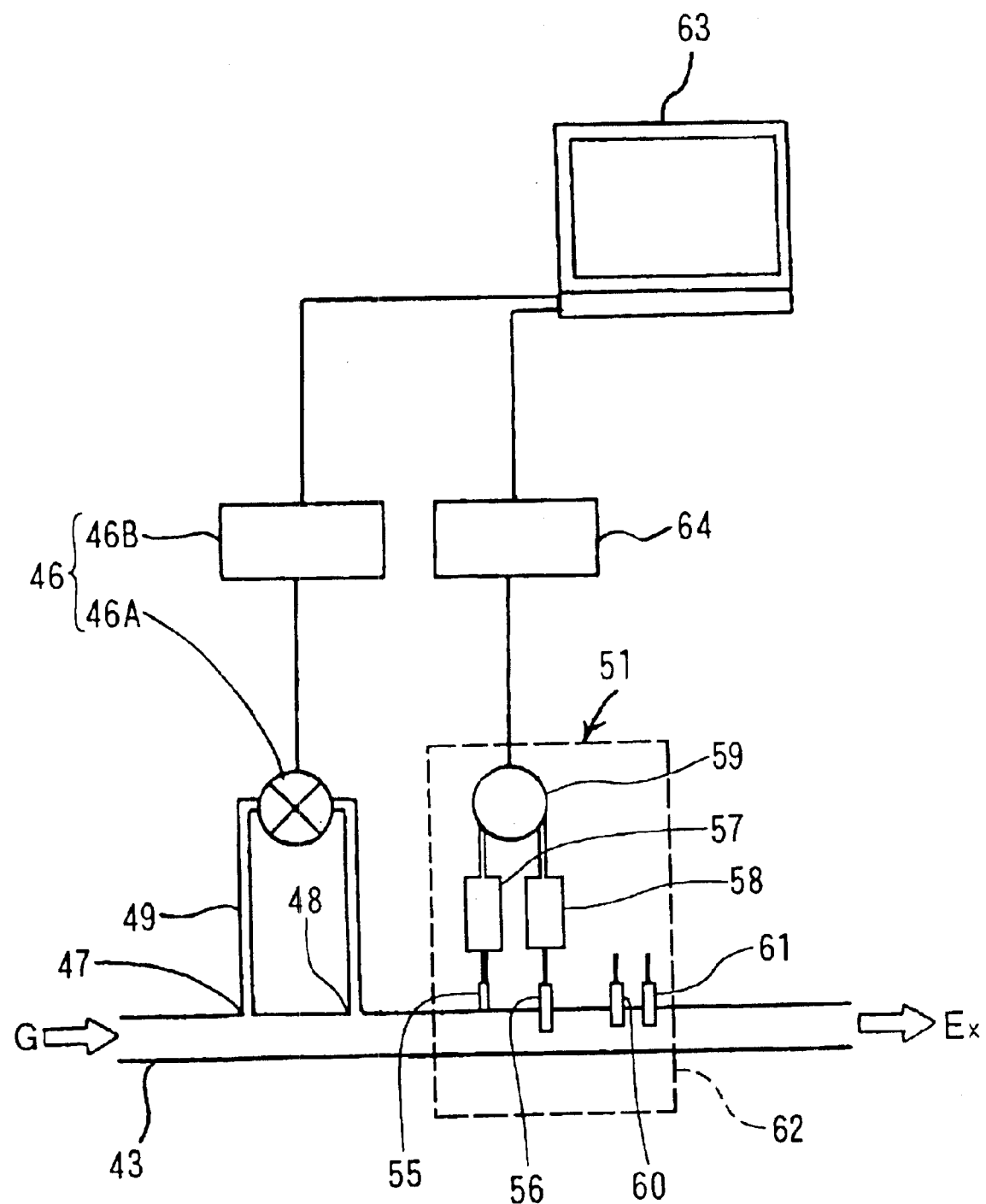
FIG. 13 is a view schematically showing one exemplary configuration of said vehicle-installed exhaust gas analyzing apparatus.
Figure 14A:
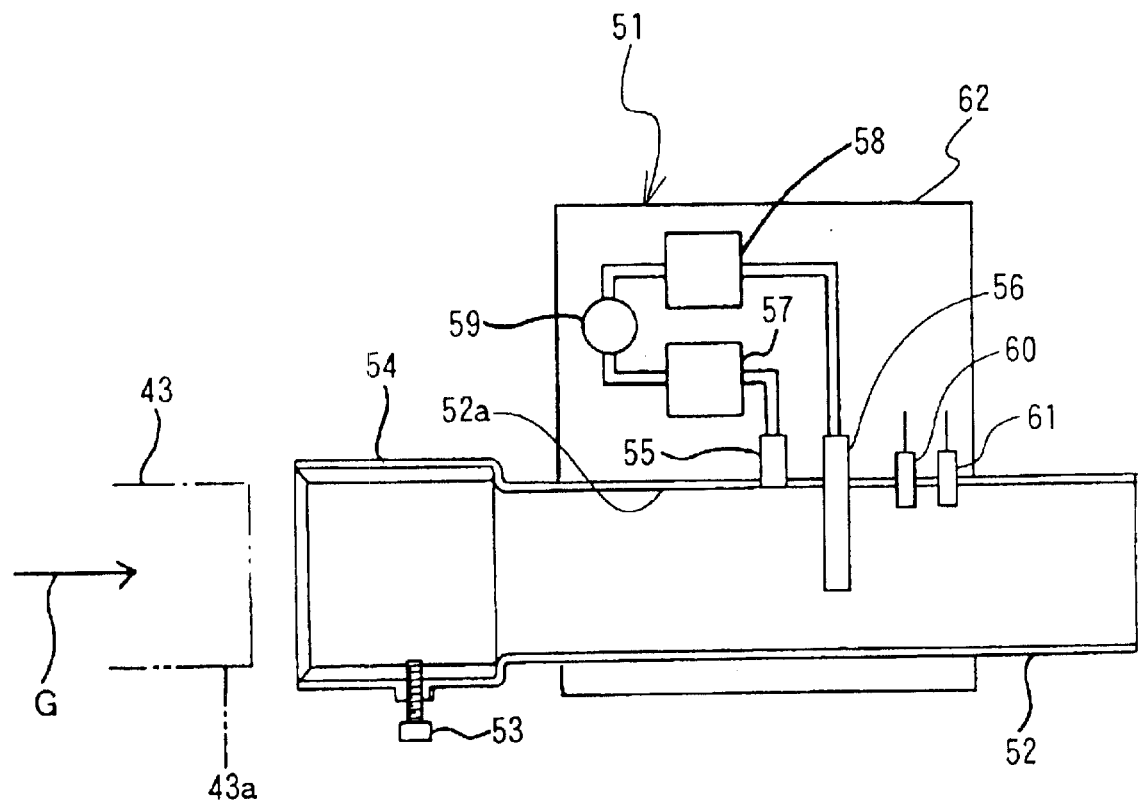
FIGS. 14(A) and (B) are an explanatory view and a perspective view schematically showing one example of an installation structure of a Pitot tube type flowmeter to an exhaust pipe used in said vehicle-installed exhaust gas analyzing apparatus.
Figure 14B:
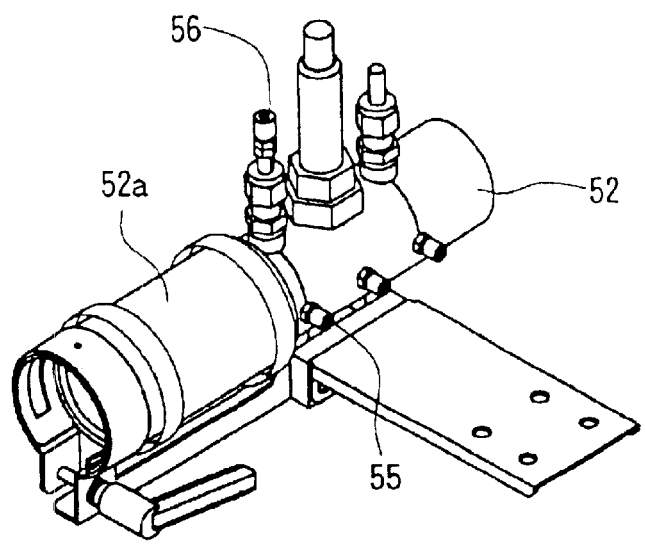

Next, the detail of another embodiment of the present invention will be explained with reference to the drawings. FIGS. 12 to 14 show one example of a vehicle-installed exhaust gas analyzing apparatus according to the present invention. First FIG. 12 shows an embodiment in which said vehicle-installed exhaust gas analyzing apparatus is installed in an automobile, and in this view, the reference numeral 41 denotes an automobile serving as a vehicle to be subjected to measurement. The reference numeral 42 denotes an engine of the automobile 41, the numeral 43 denotes an exhaust pipe connecting with the engine 42 and through which an exhaust gas G flows, the numeral 44 denotes a catalyst device provided for the exhaust pipe 43. The numeral 45 denotes a road surface.

The numeral 46 denotes an NDIR type gas analyzing device serving as an exhaust gas concentration measuring device provided within the automobile 41, which comprises a gas analyzing section 46A and an operation controlling section 46B. More specifically, as shown in FIG. 13, a gas branching section 47 and a gas converging section 48 are disposed at, for example, downstream of the catalyst device 44 in the exhaust pipe 43, and the gas analyzing section 46A is intervened in a gas flow path 49 connecting these gas branching section 47 and the gas converging section 48. The gas branching section 47 is arranged to collect a part of the exhaust gas G from the engine 42 flowing through the exhaust pipe 43 as a sample gas. A heater 50 is wound around the gas flow path 49 between the gas branching section 47 and the gas analyzing section 46A, so that the sample gas flowing therethrough is heated and kept at a predetermined temperature. Although details of structure are not shown in the drawing, the gas analyzing section 46A comprises a cell to which a part of the exhaust gas G is continuously supplied as a sample gas, the cell including an infrared light source at its one end and a detecting section for detecting concentrations of plural components to be measured, for example, HC, CO and $H_2O$ which is an interfering component via a light chopper at its other end. The operation controlling section 46B is configured to control individual sections of the gas analyzing section 46A in response to instructions from the operation processing device in the automobile 41 (described later), and to perform calculation of concentration based on output signals of the detecting section of the gas analyzing section 46A.

The numeral 51 denotes a Pitot tube type flowmeter which is detachably attached to utmost downstream end of the exhaust pipe 43 through which the exhaust gas G from the engine 42 flows, for measuring flow rate of the exhaust gas. The Pitot tube type flowmeter 51 is configured as described in FIGS. 13, 14(A) and (B). That is, in these drawings, the numeral 52 denotes a tailpipe attachment which is detachably connected to the downstream end 43a of the exhaust pipe 43 and having an inner diameter similar to that of the exhaust pipe 43 and formed at its one end with a connecting section 54 which is provided with a fixing screw 53 and is detachable fitted outside the downstream end 43a and opened at its other end. This tailpipe attachment 52 is provided with the Pitot pipe type flowmeter 51 in unit structure. That is, a Pitot tube for static pressure detection 55 is provided at the upstream position of the tailpipe attachment 52 on a tube wall 52a so as to oppose to the interior of the pipe, and a Pitot tube for dynamic pressure detection 56 is provided at a position slightly downstream the Pitot tube for static pressure detection 55 so as to be inserted in the pipe. These Pitot tubes 55 and 56 are respectively connected to a differential manometer 59 via buffer tanks 57 and 58. The numerals 60 and 61 respectively denote a temperature sensor and a pressure sensor for measuring temperature and pressure of the exhaust gas G, which are disposed so as to be inserted into the tube of the tailpipe attachment 52 at the downstream of the Pitot tube for dynamic pressure detection 56. Output signals of these sensors are inputted into an operation processing device 63 (described later) via an interface 64 (described later). The reference numeral 62 denotes a casing for accommodating the aforementioned members 55 to 61, and is attached in detachable manner to the tailpipe attachment 52 by way of suitable means.

The reference numeral 63 denotes an operation processing device (such as personal computer) installed within the automobile 41, which sends/receives a signal with said operation controlling section 46B to control the entire NDIR type gas analyzer 46, or performs operation based on signals from operation controlling section 46B and the Pitot tube type flowmeter 51 to calculate mass Mx (t) of a specific component x to be measured such as HC, CO and the like emitted from the engine 42, or displays various measurement results, or stores measurement results as data. The reference numeral 64 denotes an interface interposed between the Pitot tube type gas flowmeter 51 and the operation processing device 59, which is equipped with a function of converting an analog signal to a digital signal and so on. The operation processing device 59 is so configured that vehicle data such as vehicle speed, engine revolutions and the like in the automobile 41 is transmitted.

Herein, the expression for determining total mass emission of a specific component x using exhaust gas flow rate by the Pitot tube type flowmeter 51 and concentration of a specific component to be measured by the NDIR type gas analyzing device 46 is as follows.

First, exhaust gas flow rate (in terms of normal state) $Q_{exh}$ (t) [m³/min] can be represented by the following formula (4):

$$Q_{exh}(t) = K \times \sqrt{\frac{P_{exh}(t)}{101.3} \times \frac{293.15}{T_{exh}(t)} \times \frac{\Delta h(t)}{\gamma_{exh}}} \quad (4)$$

(wherein K: proportion coefficient $P_{exh}$ (t): exhaust gas pressure [kPa]

$T_{exh}$ (t): exhaust gas temperature [° K]

$\Delta h$ (t): differential pressure of Pitot tube $\gamma_{exh}$: exhaust gas density in normal state [g/m³]

That is, by determining the proportion coefficient K in advance, it is possible to obtain a flow rate of the gas from the temperature, pressure of the gas flowing through the pipe and measurement value of differential pressure of the Pitot tube.

Next, time-series mass emission of a component to be measured is calculated from emission concentration, exhaust gas flow rate, and density of the individual component to be measured. Specifically, emission mass (time-series) of component x [g/s] and total mass emission $M_{x\ total}$ [g/km] of component x can be represented by the following formulas (5) and (6).

$$M_x(t)C_x(t) \times 10^{-6} \times [Q_{exh}(t)/60] \times \gamma_x \quad (5)$$

$$M_x\ total = \Sigma[M_x(t)/L] \quad (6)$$

(wherein $C_x$ (t): concentration (time-series) of component x [ppm/ppmC]

$Q_{exh}$ (t): flow rate of emission gas (in terms of normal state) [m³/min]

$\gamma_x$: density of component x in normal state [g/m³]

L: driving distance of vehicle [km])

In the vehicle-installed engine exhaust gas analyzing apparatus configured as described above, a part of the exhaust gas G from the engine 42 is sampled at the gas branching section 47 of the exhaust pipe 43 and continuously supplied to the gas analyzing section 46A of the NDIR type gas analyzing device 46, whereby concentrations of HC and CO contained in the exhaust gas G are measured. The part of the exhaust gas G supplied to the gas analyzing section 46A converges at the gas converging section 48 of the exhaust tube 43 with a major part of the exhaust gas G not sampled at the gas branching section 47, and the exhaust gas G after converging then flows toward the Pitot tube type flowmeter 51 provided at the tailpipe attachment 52 connected with the downstream end of the exhaust pipe 46.

In the above Pitot tube type flowmeter 51, a static pressure of the exhaust gas G flowing in the tailpipe attachment 52 via the exhaust pipe 43 is obtained by the Pitot tube for static pressure detection 55, and a sum of dynamic pressure and static pressure of the exhaust gas G is obtained by the Pitot tube for dynamic pressure detection 56. Then, the differential manometer 59 calculates a difference between the pressure detected by the Pitot tube for static pressure detection 55 and the pressure detected by the Pitot tube for dynamic pressure detection 56 to obtain a dynamic pressure of the exhaust gas G, and flow rate of the exhaust gas G is determined by performing operation based on this dynamic pressure. And, in this case, since the pressures detected by the Pitot tube for static pressure detection 55 and by the Pitot tube for dynamic pressure detection 56 are inputted into the differential manometer 59 via the buffer tanks 57, 58, respectively, even if the exhaust gas G pulses to cause pressure change, the variation is eliminated by the buffer tanks 57 and 58, so that it is possible to derive only a pressure difference generated by change in flow rate of the exhaust gas G. Therefore, even when the exhaust gas G pulses due to change in output of the engine 42, this influence can be successfully eliminated, and flow rate of the exhaust gas G can be measured with high accuracy.

As described above, in the vehicle-installed exhaust gas analyzing apparatus in this embodiment, it is possible to continuously measure concentration of HC, CO or the like contained in the exhaust gas G emitted from the engine 42 by means of the NDIR type gas analyzing device 46, as well as to continuously measure flow rate of the exhaust gas G by the Pitot tube type flowmeter 51. Therefore, it is possible to continuously determine mass of HC and CO emitted from the engine 42 by calculation from the HC concentration and flow rate of the exhaust gas.

The Pitot tube type flowmeter 51 is disposed to the tailpipe attachment 52 which is freely and readily detachable with respect to the exhaust pipe 43 connecting to the engine 42 of the automobile 41, so that it is small and compact in shape. Furthermore, as is in the above embodiment, since the buffer tanks 57 and 58 are provided between the differential manometer 59, and the Pitot tube for static pressure detection 55 and the Pitot tube for dynamic pressure detection 56, even if pulsation occurs in the exhaust gas G flowing through the exhaust pipe 43, the flow rate of the exhaust gas G can be continuously measured with high accuracy without affected by such pulsation.

Figure 15:
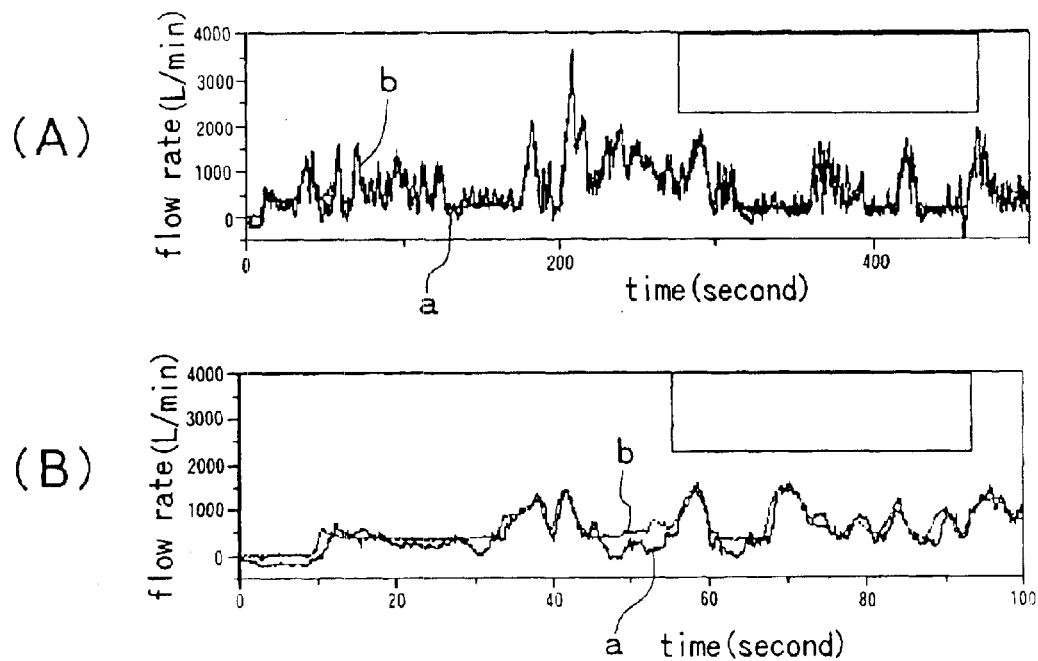
FIG. 15 is a view showing a measurement result of flow rate when buffer tanks are not provided in said vehicle-installed exhaust gas analyzing apparatus.
Figure 16:
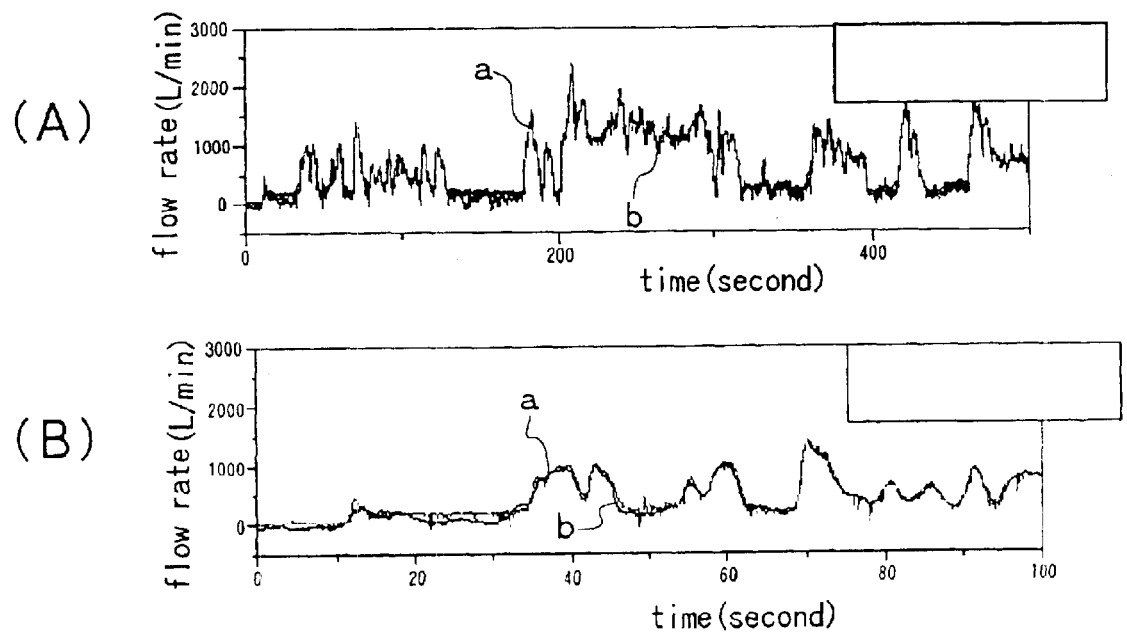
FIG. 16 is a view showing a measurement result of flow rate when buffer tanks are provided in said vehicle-installed exhaust gas analyzing apparatus.

FIGS. 15 and 16 respectively show results of flow rate measurement when the buffer tanks 57 and 58 are provided and are not provided in the Pitot tube type flowmeter 51. In these drawings, the graph denoted by the symbol A shows a result of measurement of the Pitot tube type flowmeter 51, and the graph denoted by the symbol B shows a result of measurement of the flowmeter using SAO (Smooth Approach Orifice) provided for comparison by illustration. The used automobile 41 was a gasoline car of 2L displacement. In both of FIGS. 15 and 16, (B) is a partial enlarged view of (A).

FIG. 15 shows change in flow rate when the buffer tanks 57 and 58 are not provided, and it seems that there is little difference between a and b in the graphs a and b shown in FIG. 15(A), however a considerable difference between graph a and graph b can be seen when enlarged as is (B).

FIG. 16 shows change in flow rate when the buffer tanks 57 and 58 are provided, and it seems that almost no difference can be seen between the graphs a and b.

As described above, according to the vehicle-installed exhaust gas analyzing apparatus of the present invention, the Pitot tube type flowmeter for measuring flow rate of exhaust gas flowing through the exhaust pipe connecting to the engine, the exhaust gas concentration measuring device for measuring concentration of THC in the exhaust gas, and the operation processing device are installed in the vehicle, and in the operation processing device, emission mass of the THC is continuously determined by using output signals of the Pitot tube type flowmeter and the exhaust gas concentration measuring device, as well as an exhaust gas temperature signal and an exhaust gas pressure signal. Therefore, it is not necessary to provide a trace gas source and a device for measuring the amount of injected trace gas in a vehicle, so that it is possible to continuously measure the mass of THC contained in the exhaust gas with high accuracy by simple configuration.

Additionally, when buffer tanks are provided between the differential manometer, and the Pitot tube for static pressure detection and the Pitot tube for dynamic pressure detection, even if pulsation occurs in the exhaust gas, a variation of pressure varying due to this pulsation is eliminated by the buffer tanks, so that the influence of the pulsation can be successfully eliminated. Furthermore, since the Pitot tube for static pressure detection and the Pitot tube for dynamic pressure detection are provided in the tailpipe attachment which is freely connected/disconnected with the exhaust pipe, these members can be easily handled, and attachment and detachment to/from the exhaust tube can be easily conducted.

Figure 17:
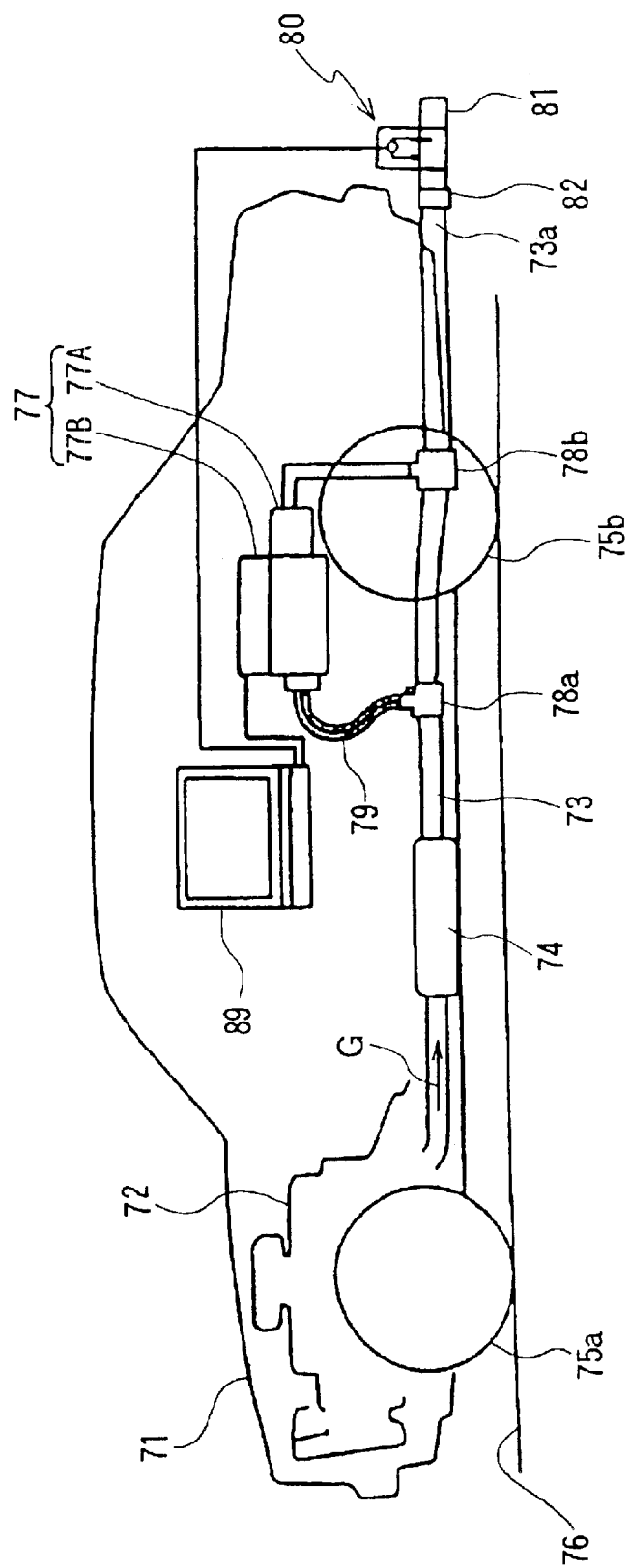
FIG. 17 is a view showing an embodiment wherein a differential pressure type flowmeter according to the present invention is installed in an automobile together with an exhaust gas concentration measuring device to configure a vehicle-installed engine exhaust gas analyzing apparatus.
Figure 18:
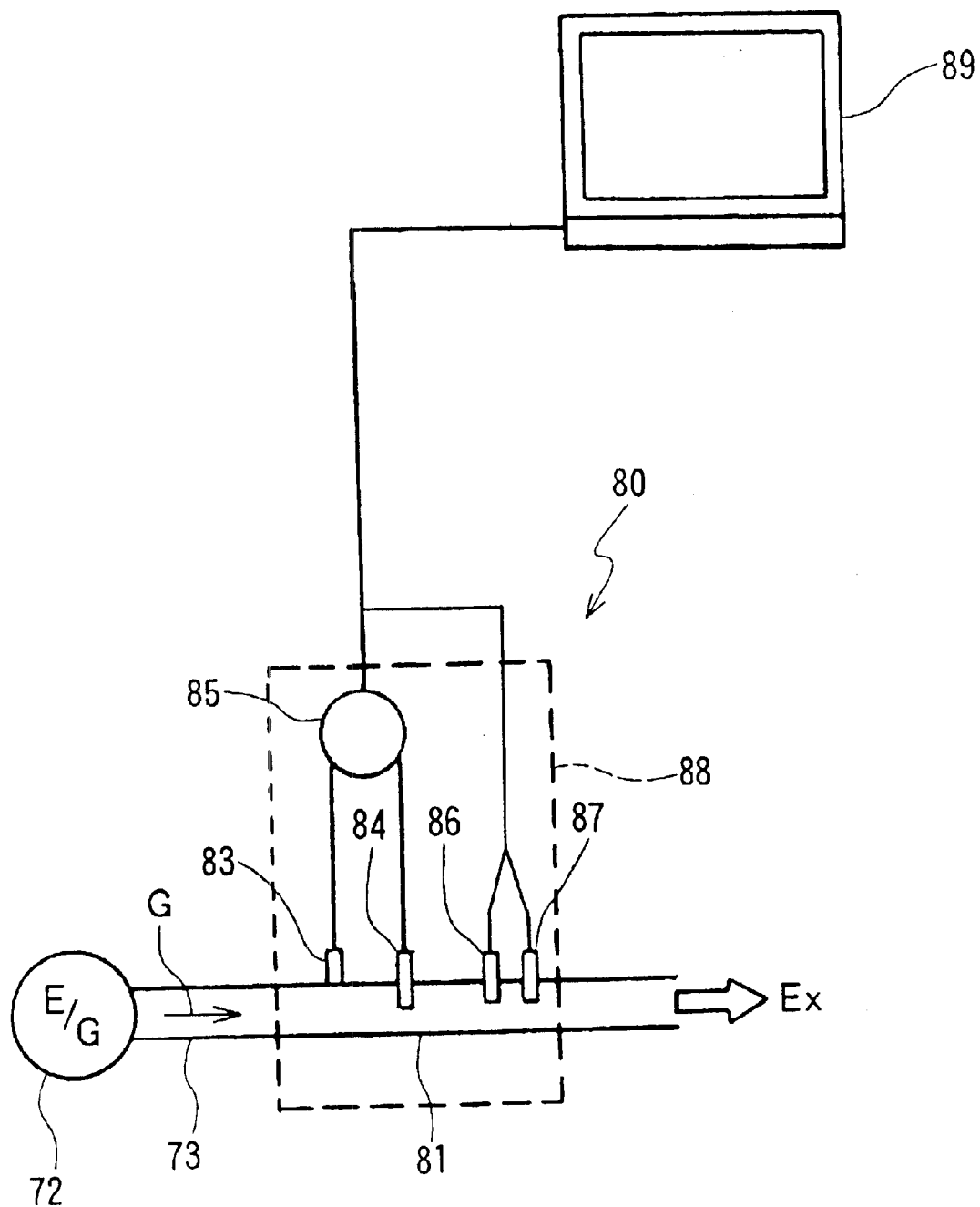
FIG. 18 is a view schematically showing a principal part of said differential pressure type flowmeter.

In the following, the detail of another embodiment of the present invention will be explained with reference to the drawing. FIG. 17 shows an embodiment in which a differential pressure type flowmeter is installed in an automobile together with an exhaust gas concentration measuring device to configure the vehicle-installed engine exhaust gas analyzing apparatus. FIG. 18 schematically shows configuration of a principal part of the differential pressure type flowmeter. First, in FIG. 17, the reference numeral 71 denotes an automobile to be subjected to measurement, the numeral 72 denotes an engine of the automobile 71, the numeral 73 denotes an exhaust pipe connecting with the engine 72 and through which an exhaust gas G flows, the numeral 74 denotes a catalyst device provided for the exhaust pipe 73. The numerals 75a and 75b respectively denote a front wheel and a rear wheel. The numeral 76 denotes a road surface.

In FIG. 17, the numeral 77 denotes an NDIR (non-dispersive type infrared) type gas analyzing device serving as an exhaust gas concentration measuring device provided within the automobile 71, which comprises a gas analyzing section 77A and an operation controlling section 77B. The gas analyzing section 77A is intervened in a gas flow path 79 whose one end is connected to the exhaust pipe 73 via a gas branching section 78a and other end is connected to the exhaust pipe 73 via a gas converging section 78b. Although details of structure are not shown in the drawing, the gas analyzing section 77A comprises a cell to which a part of the exhaust gas G is continuously supplied as a sample gas, the cell including an infrared optical source disposed at one end thereof, and a detecting section for detecting concentrations of a plurality of components to be measured e.g., HC, CO and $H_2O$ which is an interfering component via an optical chopper at the other end thereof. The operation controlling section 77B is arranged to control individual sections of the gas analyzing section 77A in response to instructions from the operation processing device 89 in the automobile 71 (described later), and to perform calculation of concentration based on output signals of the detecting section.

In FIG. 17, the numeral 80 denotes a differential pressure type flowmeter which is detachably attached to utmost downstream end of the exhaust pipe 73, for measuring flow rate of the exhaust gas. In this embodiment, the differential pressure type flowmeter is implemented by a Pitot tube type flowmeter and configured as follows. That is, in these drawings, the numeral 81 denotes a tailpipe attachment which is detachably connected to the downstream end of the exhaust pipe 73 and having an inner diameter similar to that of the exhaust pipe 73, the tailpipe attachment 81 being formed at its one end with a connecting section 82 with respect to the downstream end of the exhaust pipe 73 and open at its other end. This tailpipe attachment 81 is provided with a Pitot tube for static pressure detection 83 and a Pitot tube for dynamic pressure detection 84 of the Pitot tube type flowmeter 80, and these Pitot tubes 83 and 84 are respectively connected to a differential manometer 85. The numerals 86 and 87 respectively denote a temperature sensor and a pressure sensor for measuring temperature and pressure of the exhaust gas G, which are disposed so as to be inserted into the tube of the tailpipe attachment 81 at the downstream of the Pitot tube for dynamic pressure detection 84. Output signals of the differential manometer 85, temperature sensor 86 and pressure sensor 87 are inputted into an operation processing device 89. The reference numeral 88 denotes a casing for accommodating the aforementioned members 83 to 87 in integrated manner, and is detachably attached to the tailpipe attachment 81 by way of suitable means.

In FIGS. 17 and 18, the reference numeral 89 denotes an operation processing device (such as personal computer) installed within the automobile 71, which sends/receives a signal with said operation controlling section 77B to control the entire NDIR type gas analyzing device 77, or performs operation based on signals from operation controlling section 77B and the Pitot tube type flowmeter 80 to calculate mass of a specific component to be measured such as HC, CO and the like emitted from the engine 72, or displays various measurement results, or stores measurement results as data. The operation processing device 89 is so configured that vehicle data such as vehicle speed, engine revolutions and the like in the automobile 71 is transmitted.

In the vehicle-installed engine exhaust gas analyzing apparatus configured as described above, a part of the exhaust gas G from the engine 72 is sampled at the gas branching section 78a of the exhaust pipe 73 and continuously supplied to the gas analyzing section 77A of the NDIR type gas analyzing device 77, whereby concentrations of HC, CO and $H_2O$ contained in the exhaust gas G are measured. The part of the exhaust gas G supplied to the gas analyzing section 77A converges at the gas converging section 78b of the exhaust tube 73 with a major part of the exhaust gas G not sampled at the gas branching section 78a, and the exhaust gas G after converging then flows toward the Pitot tube type flowmeter 80 provided at the tailpipe attachment 81 connected with the downstream end of the exhaust pipe 73.

In the above Pitot tube type flowmeter 80, a static pressure of the exhaust gas G flowing in the tailpipe attachment 81 via the exhaust pipe 73 is obtained by the Pitot tube for static pressure detection 83, and a sum of dynamic pressure and static pressure of the exhaust gas G is obtained by the Pitot tube for dynamic pressure detection 84. Then, the differential manometer 85 calculates a difference between the pressure detected by the Pitot tube for static pressure detection 83 and the pressure detected by the Pitot tube for dynamic pressure detection 84 to obtain a differential pressure signal representing a dynamic pressure of the exhaust gas G. In the present invention, the differential pressure signal is processed at the operation processing device 89 in the following manner, whereby flow rate of the exhaust gas G is obtained. In the following, a processing method of the differential pressure signal will be explained in detail with reference to FIGS. 19 and 20.

Figure 19:
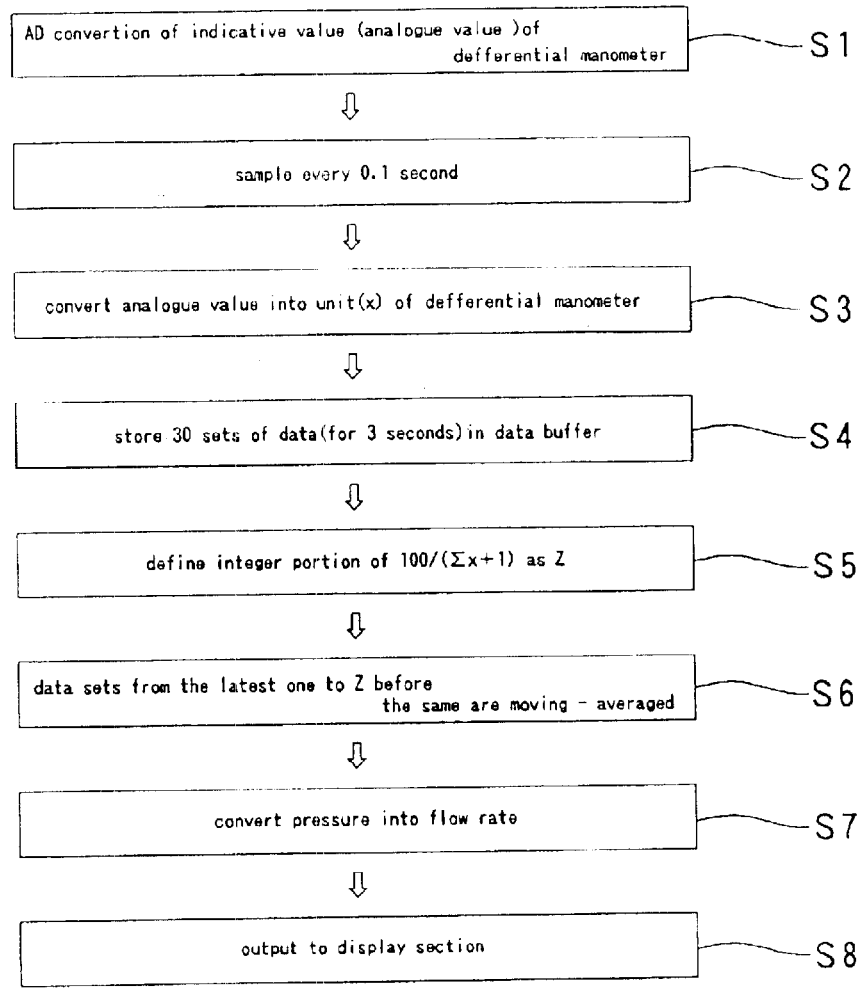
FIG. 19 is a flow chart showing one example of a processing procedure carried out in said differential pressure type flowmeter.

FIG. 19 is a flow chart showing one example of a processing procedure carried out at the operation processing device 89.

Since the differential pressure signal (indication value) inputted from the differential manometer 85 to the operation processing device 89 is an analogue value, this analogue value is subjected to AD conversion (step S1)

Then the data after AD conversion is sampled every 0.1 second (step S2).

An analogue value is converted into an amount represented by a unit (for example, kPa) of the differential manometer 85, and the magnitude of this data is defined as x (step S3).

30 sets of data having subjected to unit conversion (in this example, data sets for 3 seconds) are stored in a data buffer of CPU of the operation processing device 89 (step S4).

A sum of 30 sets of data represented by the above unit, namely $\Sigma x$ is calculated, added with 1, and an arbitrary number Y (for example 100) is divided by the resultant ($\Sigma x+1$), to determine integer portion Z (step S5). The arithmetic expression of the above process is represented by the following formula (8):

$$Z = 100/(\Sigma x + 1) \qquad (8)$$

Among the data sets stored in the above data buffer, data sets from the latest one to Z before the same are moving-averaged as shown by the following formula (9) (step S6), to determine pressure $\Delta H$ after moving-average.

$$\Delta H = \sum_{i=0}^{z-1} X_i / Z \qquad (9)$$

The pressure obtained by the above formula (9) is converted into flow rate using the above formula (7) (step S7), and the result is displayed on a display section of the operation processing device 89 (step S8).

Figure 20:
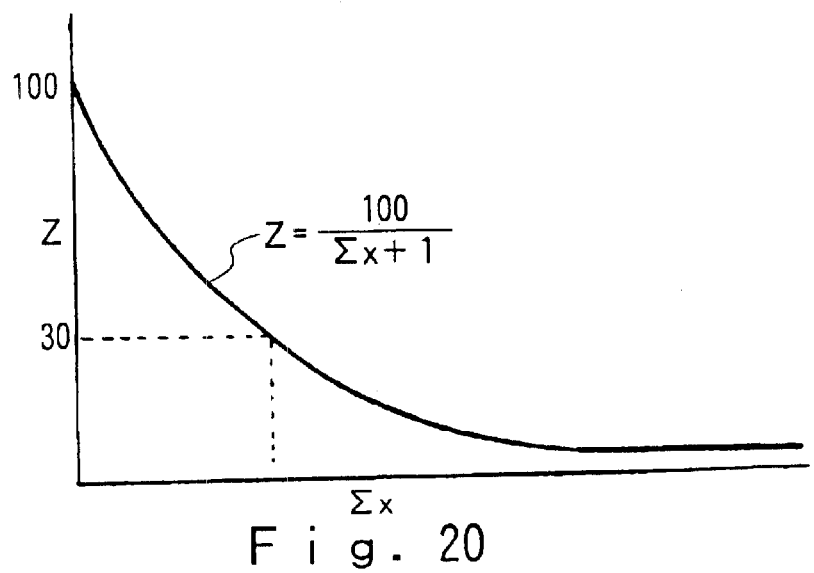
FIG. 20 is a view for explaining moving average performed in said differential pressure type flowmeter.

As described above, in the differential pressure type flowmeter of the present invention, the differential pressure signal obtained in the differential manometer 85 is sampled every certain time, for example, every 0.1 second, to thereby usually store a predetermined number of data sets, and in moving-averaging these sampled plural data sets, the number of data set Z to be used for the moving-average is determined by using the above formula (8). Therefore, the value of x is smaller in low flow rate zone than in high flow rate zone, and thus the sum of $x, \Sigma x$ is smaller in low flow rate zone than in high flow rate zone, so that Z in the above formula (8) becomes larger in low flow rate zone than in high flow rate zone. The above Z is represented by the curve as shown in FIG. 20, for example.

That is, in the differential pressure type flowmeter of the present invention, in moving-averaging plural sets of sampled data, it is possible to change the number of data set to be subjected to the moving-average in real time depending on low flow rate zone and high flow rate zone. More specifically, the number of data set to be used in the moving-average is larger in low flow rate zone where S/N is small than in high flow rate zone where S/N is large. As a result of this, a wide flow rate range is realized without decreasing the response speed in high flow rate zone where influence is large when calculating the emission amount of exhaust gas component from exhaust gas flow rate as is the case of engine exhaust gas analysis, for example. Furthermore, since the number of data used for moving-average is large in low flow rate zone and the number of data used for moving-average is small in high flow rate zone, even if pulsation occurs in the gas flow to cause variation of differential pressure, by taking data of longer than the cycle of the variation, it is possible to eliminate the influence caused by the variation in differential pressure.

Figure 21:
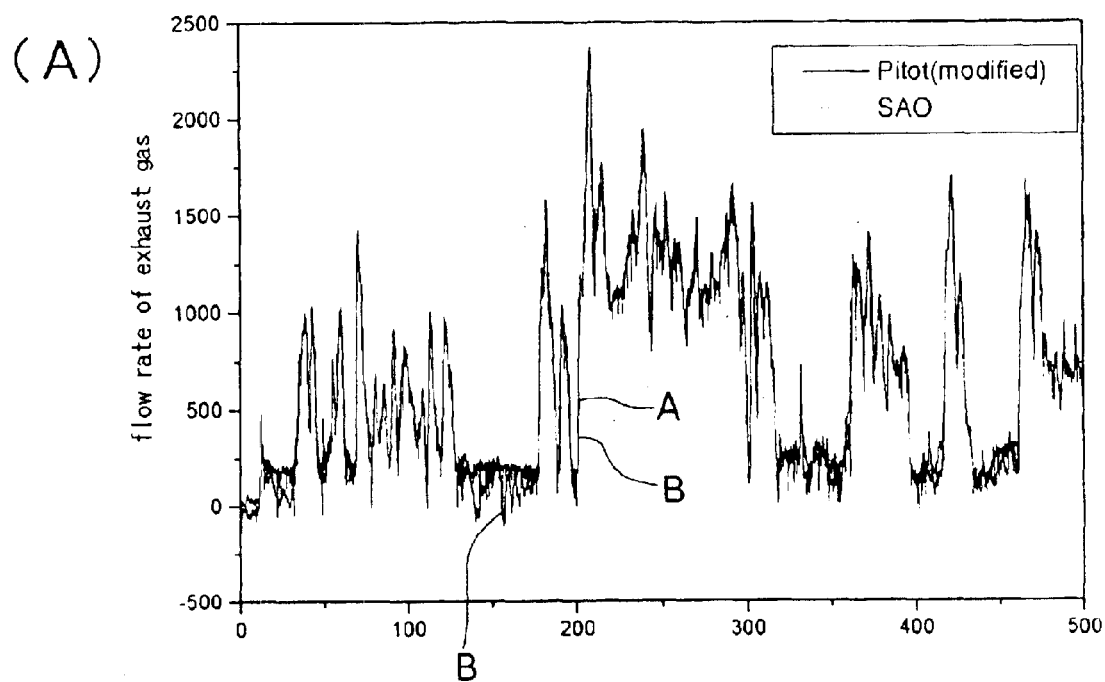
FIG. 21 is a view for explaining characteristics of said differential pressure type flowmeter.
Figure 21:
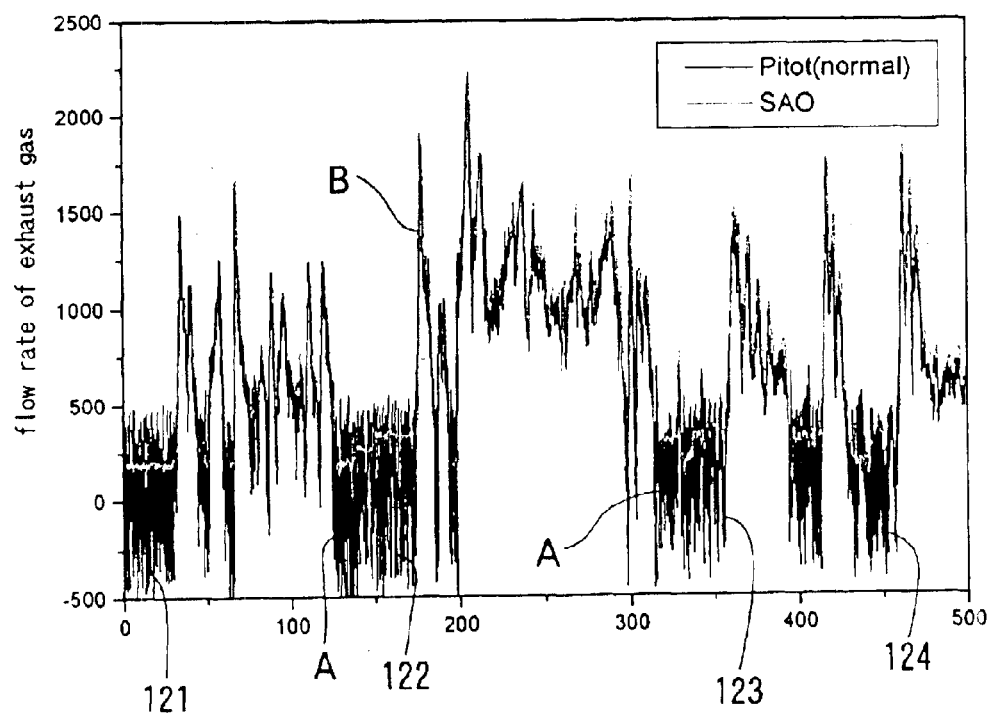

FIG. 21 is a view for explaining characteristics of the differential pressure type flowmeter having the above configuration. FIG. 21(A) shows temporal change of exhaust gas flow rate when calculation is executed while conducting moving-average varying in real time based on the above formulas (8) and (9), and FIG. 21(B) shows temporal change of exhaust gas flow rate when calculation is executed without conducting moving-average varying. In both of (A) and (B), the curve denoted by the symbol A shows a measurement result of exhaust gas flow rate using the Pitot tube type flowmeter, and the curve denoted by the symbol B shows a measurement result of exhaust gas flow rate using SAO (Smooth Approach Orifice).

Figure 22:
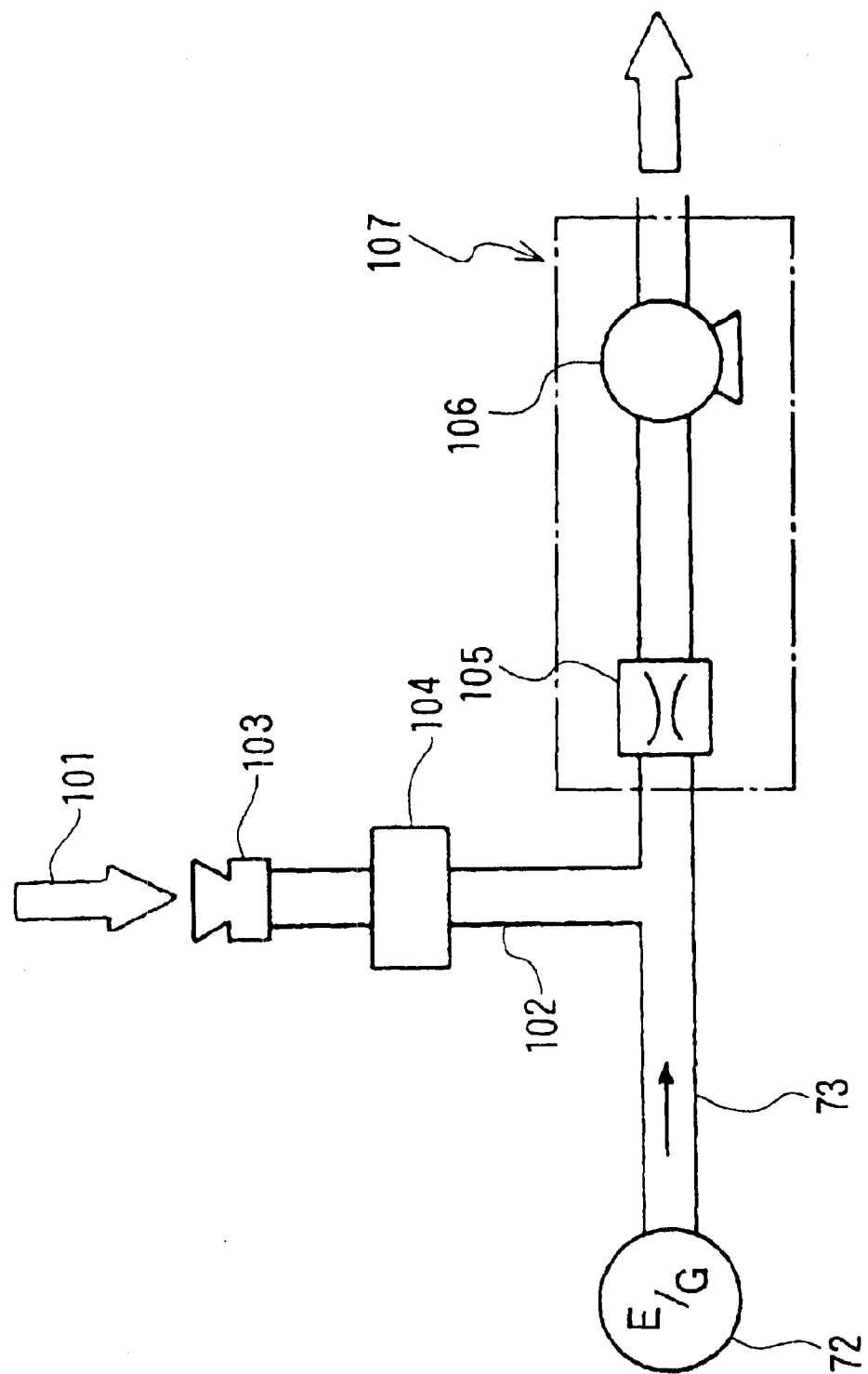
FIG. 22 is a view schematically showing one exemplary configuration when flow rate is measured using Smooth Approach Orifice (SAO).

As shown, for example, in FIG. 22, the SAO is configured as follows: a dilution air introducing tube 102 for introducing dilution air 101 is connected to the exhaust pipe 73 connecting to the engine 72; a SAO 103 and an air filter 104 are connected from upstream to the dilution air introducing tube 102; at downstream side from the connection between the exhaust pipe 73 and the dilution air introducing tube 102 is provided a CVS device (constant volume sampling device) 107 including a CFV (critical flow venture) 105 and blower 106 for measuring the amount of dilution air; and exhaust gas flow rate is determined based on a difference between the dilution air amount and the total flow of the CFV 105.

FIGS. 21(A) and (B) revealed the following findings: the flow rate of exhaust gas when calculation is executed without conducting moving-average largely changes in low flow rate zone of 250 L/min or less, for example, and in particular, at flow rates around 0, a considerable noise appears due to pulsation of the engine 72 and noise of the pressure meter 80. In addition, negative flow rate values are observed as indicated by the numerals 121 to 124, although a flow rate never takes a negative value. To the contrary, in the exhaust gas flow rate when calculation is executed while conducting moving-average which varies in real time, as shown in FIG. 21(A), the influence by the noise at flow rates around 0 is almost eliminated without decreasing the rate of rise. Additionally, the problem that the flow rate takes a negative value is also solved.

As described above, in the differential pressure type flowmeter of the present invention, a differential pressure signal outputted from the differential manometer 85 is sampled every certain time, and the latest predetermined number of data are usually stored, and in moving-averaging these sampled plurality of data for improving S/N, the number of data to be subjected to moving-average is varied in real time depending of the flow rate between low flow rate are and high flow rate zone. Therefore, a wide flow rate range is realized without decreasing the response speed in high flow rate zone where influence is large when calculating the emission amount of exhaust gas component from exhaust gas flow rate as is the case of engine exhaust gas analysis, for example.

Furthermore, when calculation is executed as shown by the formulas (8) and (9) in moving-averaging the sampled plurality of data for improving S/N, the number of data used for moving-average is large in low flow rate zone and the number of data used for moving-average is small in high flow rate zone, so that even if pulsation occurs in the gas flow to cause variation of differential pressure, by taking data of longer than the cycle of the variation, it is possible to eliminate the influence caused by the variation in differential pressure. This is especially advantageous for continuous measurement of gas wherein pressure largely varies due to pulsation because of low flow rate, as is in idle state.

In the embodiment as described above, the differential pressure in the gas flowing through the pipe is detected by using the Pitot tube type flowmeter 80, flowmeters of venturi type or laminar flow type may be used as the differential pressure detecting means.

The present invention is suitable for continuously measuring flow rate of gas in which a measuring range of flow rate is wide and change (variation) in flow rate is large, as is exhaust gas from automobile engine, as discussed above. It goes without saying that the present invention is also applicable to continuous measurement of flow rate of exhaust gas other than the above exhaust gas, for example, exhaust gas from combustion equipment such as boiler.

By the way, when the range of flow rate to be measured is about 100 times (for example, when measuring from 20 L/min to 2000 L/min), the differential manometer is requested to have such accuracy capable of accurately measuring 1/1000 (0.01% with respect to the full scale of differential pressure). Actually, it is difficult to accurately measure the differential pressure of 0.01% of full scale. For this reason, in the present embodiment, when a differential manometer capable of accurately measuring 1/Po of full scale, for example, the arbitrary number Y which is set at 100 in the above formula (8) and the number of the latest data n usually stored in the data buffer are approximately calculated in the following manner.

That is, in this embodiment, the number of times of moving-average (Z) is preciously defined as follows:

$$Z = \left[ \frac{Y}{\sum_{i=1}^{n} X_i + 1} \right] \quad ([\,]: \text{Gauss symbol}) \tag{10}$$

(wherein x represents a differential pressure measured at ith times).

Assuming that the full scale of the differential manometer is A (kPa), when the differential pressure is $(1/P_o)A$ or more, that is, the average value of xi is $(1/P_o)A$, (in other words, $$\sum_{i=1}^{n} X_i = \frac{nA}{P_o} \Bigg),$$

In the following formula is established so as not to conduct moving-average.

$$\frac{Y}{\frac{nA}{P_o} + 1} \leq 1 \tag{11}$$

Therefore, Y is defined by:

$$Y \leq \frac{nA}{P_o} + 1 \tag{12}$$

Then Y and n may be defined so that they satisfy the formula (12) and can satisfy the required flow rate accuracy even when the differential pressure is low.

In some cases, the portion of C may be replaced by other constant or the Σ portion may be squared to weigh the area around zero point as shown by the following formulas (13) and (14).

$$Z = \left[ \frac{Y}{\sum_{i=1}^{n} X_i + C} \right] \quad ([\,]: \text{Gauss symbol}) \tag{13}$$

$$Z = \left[ \frac{Y}{\left( \sum_{i=1}^{n} X_i \right)^2 + C} \right] \quad ([\,]: \text{Gauss symbol}) \tag{14}$$

As explained above, according to the differential pressure type flowmeter of the present invention, it is possible to continuously measure the gas flow rate while securely reducing the noise in low flow rate zone without decreasing the response speed in high flow rate zone, or at a desired response speed and with high accuracy over the wide measuring range from low flow rate zone to high flow rate zone.

What is claimed is:

1. A vehicle-installed exhaust gas analyzing apparatus comprising:

a nondispersive infrared (NDIR) type gas analyzer installed in the vehicle for continuously measuring concentration of hydrocarbon (HC) in an exhaust gas flowing through an exhaust pipe which is connected to an engine;

an exhaust gas flowmeter installed in the vehicle for continuously measuring flow rate of the exhaust gas flowing through the exhaust pipe; and an operation processing device installed in the vehicle for processing outputs from the NDIR type gas analyzer and the exhaust gas flowmeter to continuously calculate mass of total hydrocarbon (THC) contained in the exhaust wherein THC concentration is obtained by multiplying a measurement result obtained by the NDIR type analyzer by a predetermined conversion factor.

2. The vehicle-installed exhaust gas analyzing apparatus according to claim 1, wherein a Pitot tube type flowmeter is used as said exhaust gas flowmeter, and said operation processing device is configured to continuously calculate said mass emission of THC using respective output signals of said Pitot tube type flowmeter and NDIR type analyzer as well as an exhaust gas temperature signal and exhaust gas pressure signals.

3. The vehicle-installed exhaust gas analyzing apparatus according to claim 2, wherein a device for removing influence of pressure change due to pulsation is provided between a differential manometer and a Pitot tube for static pressure detection and a Pitot tube for dynamic pressure detection of the Pitot tube type flowmeter.

4. The vehicle-installed exhaust gas analyzing apparatus according to claim 2, wherein the Pitot tube type flowmeter is provided in a tailpipe attachment which is connectable/detachable to/from the exhaust pipe which is connected to the engine.

5. The vehicle-installed exhaust gas analyzing apparatus according to claim 1, wherein a differential pressure type flowmeter which is adapted to detect a differential pressure in the gas flowing through the exhaust pipe by means of a differential manometer and subject a differential pressure signal outputted from the differential manometer to an arithmetic process, thereby obtaining flow rate of the gas is used as the exhaust gas flowmeter, the differential pressure signal is sampled every certain time, a predetermined number of data is stored, and when subjecting these sampled plural data to moving-average, the number of data to be subjected to the moving-average is changed in accordance with the flow rate.

6. The vehicle-installed exhaust gas analyzing apparatus according to claim 5, wherein it defines the data obtained by converting an indicative value of the differential manometer into a pressure unit as x and an arbitrary number as Y, and data of the number corresponding to $[Y/(\Sigma x+1)]$ ($[\ ]$: Gauss symbol) is moving-averaged.

7. The vehicle-installed exhaust gas analyzing apparatus according to claim 5, wherein it defines the data obtained by converting an indicative value of the differential manometer into a pressure unit as x, an arbitrary number as Y, an appropriate integer as $\alpha$, and an appropriate constant as C, and data of the number corresponding to $[Y/(\Sigma x)^{\alpha}+C)]$ ($[\ ]$: Gauss symbol) is moving-averaged, and the number of data is automatically adjusted to a suitable value by a full scale value of the differential manometer and a flow rate of a predetermined time.

* * * * *